US012661391B2

(12) United States Patent
Kraus et al.

(10) Patent No.: US 12,661,391 B2
(45) Date of Patent: *Jun. 23, 2026

(54) COMPOSITIONS AND METHODS FOR TREATMENT OF HOMOCYSTINURIA

(71) Applicant: The Regents of the University of Colorado, Denver, CO (US)

(72) Inventors: Jan P. Kraus, Denver, CO (US); Tomas Majtan, Aurora, CO (US); Erez Bublil, Ets Efraim (IL)

(73) Assignee: The Regents of the University of Colorado, a Body Corporate, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/658,735

(22) Filed: May 8, 2024

(65) Prior Publication Data

US 2025/0041392 A1 Feb. 6, 2025

Related U.S. Application Data

(60) Continuation of application No. 17/852,246, filed on Jun. 28, 2022, now abandoned, which is a continuation of application No. 16/910,735, filed on Jun. 24, 2020, now Pat. No. 11,400,143, which is a continuation of application No. 16/243,295, filed on Jan. 9, 2019, now Pat. No. 10,729,753, which is a continuation of application No. 15/492,671, filed on Apr. 20, 2017, now Pat. No. 10,265,387, which is a continuation of application No. 14/935,690, filed on Nov. 9, 2015, now Pat. No. 9,675,678, which is a continuation-in-part of application No. 14/687,389, filed on Apr. 15, 2015, now Pat. No. 9,447,406, which is a division of application No. 13/803,804, filed on Mar. 14, 2013, now Pat. No. 9,034,318.

(60) Provisional application No. 61/758,138, filed on Jan. 29, 2013.

(51) Int. Cl.
| | |
|---|---|
| A61K 38/51 | (2006.01) |
| A61K 9/00 | (2006.01) |
| A61K 31/198 | (2006.01) |
| A61K 31/205 | (2006.01) |
| A61K 31/385 | (2006.01) |
| A61K 45/06 | (2006.01) |
| A61K 47/60 | (2017.01) |
| C12N 9/88 | (2006.01) |
| C12N 9/96 | (2006.01) |

(52) U.S. Cl.
CPC ............ *A61K 38/51* (2013.01); *A61K 9/0019* (2013.01); *A61K 31/198* (2013.01); *A61K 31/205* (2013.01); *A61K 31/385* (2013.01); *A61K 45/06* (2013.01); *A61K 47/60* (2017.08);

*C12N 9/88* (2013.01); *C12N 9/96* (2013.01); *C12Y 402/01022* (2013.01); *A61K 2300/00* (2013.01)

(58) Field of Classification Search
CPC .... A61K 38/51; A61K 9/0019; A61K 31/198; A61K 31/205; A61K 31/385; A61K 45/06; A61K 47/60; A61K 2300/00; C12N 9/88; C12N 9/96; C12Y 402/01022
See application file for complete search history.

(56) References Cited

U.S. PATENT DOCUMENTS

| | | | |
|---|---|---|---|
| 5,523,225 A | 6/1996 | Kraus | |
| 5,635,375 A | 6/1997 | Kraus et al. | |
| 5,643,575 A | 7/1997 | Martinez et al. | |
| 5,656,425 A | 8/1997 | Kraus | |
| 5,705,151 A | 1/1998 | Dow et al. | |
| 5,730,990 A | 3/1998 | Greenwald et al. | |
| 5,902,588 A | 5/1999 | Greenwald et al. | |
| 5,919,455 A | 7/1999 | Greenwald et al. | |
| 6,113,906 A | 9/2000 | Greenwald et al. | |
| 6,153,655 A | 11/2000 | Martinez et al. | |
| 6,174,696 B1 | 1/2001 | Seman | |
| 6,177,087 B1 | 1/2001 | Greenwald et al. | |
| 6,436,658 B1 | 8/2002 | Seman | |
| 6,596,701 B1 | 7/2003 | Schwartz et al. | |
| 6,638,500 B1 | 10/2003 | El-Tayar et al. | |
| 7,485,307 B2 | 2/2009 | Kraus et al. | |
| 7,816,495 B2 | 10/2010 | Kingsland et al. | |
| 8,007,787 B2 | 8/2011 | Kraus | |
| 8,398,989 B2 | 3/2013 | Kraus et al. | |
| 9,011,844 B2 | 4/2015 | Kraus | |
| 9,034,318 B2 | 5/2015 | Kraus et al. | |
| 9,243,239 B2 | 1/2016 | Carrillo et al. | |
| 9,284,546 B2 | 3/2016 | Kraus | |
| 9,447,406 B2 | 9/2016 | Kraus et al. | |
| 9,631,188 B2 | 4/2017 | Kraus | |
| 9,675,678 B2 | 6/2017 | Kraus et al. | |

(Continued)

FOREIGN PATENT DOCUMENTS

| | | |
|---|---|---|
| CA | 2898772 A1 | 8/2014 |
| CN | 1552905 A | 12/2004 |

(Continued)

OTHER PUBLICATIONS

"A novel protease for site-specific cleavage of GST fusion proteins," *Science Tools from Pharmacia Biotech* 2(1):18-19, 1997.
"Sequence alignment between SEQ ID No. 2 and AC P35520," Jun. 1, 1994, 2 pages.
Adam et al., "Dietary practices in pyridoxine non-responsive homocystinuria: A European survey," *Molecular Genetics and Metabolism* 110:454-459, 2013.

(Continued)

*Primary Examiner* — Ganapathirama Raghu

(74) *Attorney, Agent, or Firm* — Seed IP Law Group LLP

(57) ABSTRACT

Provided herein are improved compositions and methods for enzyme replacement therapy using modified human cystathionine beta synthase (CBS) in the treatment of homocystinuria and related diseases and disorders.

21 Claims, 13 Drawing Sheets

Specification includes a Sequence Listing.

(56) References Cited

U.S. PATENT DOCUMENTS

| | | | |
|---|---|---|---|
| 10,046,036 | B2 | 8/2018 | Kraus et al. |
| 10,160,962 | B2 | 12/2018 | Carrillo et al. |
| 10,265,387 | B2 | 4/2019 | Kraus et al. |
| 10,280,415 | B2 | 5/2019 | Kraus |
| 10,624,959 | B2 | 4/2020 | Kraus et al. |
| 10,653,755 | B2 | 5/2020 | Kraus et al. |
| 10,729,753 | B2 | 8/2020 | Kraus et al. |
| 10,941,392 | B2 | 3/2021 | Carrillo et al. |
| 11,077,175 | B2 | 8/2021 | Kraus et al. |
| 11,324,811 | B2 | 5/2022 | Majtan et al. |
| 11,400,143 | B2 | 8/2022 | Kraus et al. |
| 11,771,745 | B2 | 10/2023 | Kraus et al. |
| 2003/0091543 | A1 | 5/2003 | Klein et al. |
| 2004/0033219 | A1 | 2/2004 | Kraus et al. |
| 2004/0043374 | A1 | 3/2004 | DePablo et al. |
| 2005/0036981 | A1 | 2/2005 | Yagi et al. |
| 2006/0251641 | A1 | 11/2006 | Keimel |
| 2007/0010492 | A1 | 1/2007 | Generale |
| 2010/0016672 | A1 | 1/2010 | Segawa et al. |
| 2010/0166725 | A1 | 7/2010 | Kraus et al. |
| 2012/0263700 | A1 | 10/2012 | Kraus et al. |
| 2013/0251700 | A1 | 9/2013 | Carrillo et al. |
| 2014/0023630 | A1 | 1/2014 | Kraus et al. |
| 2016/0017309 | A1 | 1/2016 | Kraus |
| 2016/0222369 | A1 | 8/2016 | Kraus |
| 2017/0065687 | A1 | 3/2017 | Kraus et al. |
| 2017/0224787 | A1 | 8/2017 | Kraus et al. |
| 2017/0253865 | A1 | 9/2017 | Kraus |
| 2018/0187154 | A1 | 7/2018 | Kahvejian et al. |
| 2018/0318404 | A1 | 11/2018 | Kraus et al. |
| 2020/0261555 | A1 | 8/2020 | Majtan et al. |
| 2020/0276282 | A1 | 9/2020 | Kraus et al. |
| 2022/0125896 | A1 | 4/2022 | Kraus et al. |
| 2022/0265835 | A1 | 8/2022 | Bublil et al. |
| 2022/0290116 | A1 | 9/2022 | Sellos-Moura et al. |
| 2023/0039591 | A1 | 2/2023 | Majtan et al. |
| 2023/0042914 | A1 | 2/2023 | Kraus et al. |

FOREIGN PATENT DOCUMENTS

| | | | |
|---|---|---|---|
| CN | 101322840 | A | 12/2008 |
| CN | 102741288 | A | 10/2012 |
| CN | 105452457 | A | 3/2016 |
| CN | 108472277 | A | 8/2018 |
| EP | 1396537 | A1 | 3/2004 |
| EP | 1878739 | A1 | 1/2008 |
| JP | 2004505024 | A | 2/2004 |
| JP | 6146934 | B2 | 6/2017 |
| JP | 6453243 | B2 | 1/2019 |
| KR | 10-2018-0074703 | A | 7/2018 |
| WO | WO 9507714 | A1 | 3/1995 |
| WO | WO 0102600 | A2 | 1/2001 |
| WO | WO 0209515 | A1 | 2/2002 |
| WO | WO 03106971 | A2 | 12/2003 |
| WO | WO 2011025964 | A2 | 3/2011 |
| WO | WO 2011097381 | A2 | 8/2011 |
| WO | WO 2012001336 | A1 | 1/2012 |
| WO | WO 2013148580 | A1 | 10/2013 |
| WO | WO 2014120770 | A1 | 8/2014 |
| WO | WO 2015033279 | A1 | 3/2015 |
| WO | WO 2018195006 | A1 | 10/2018 |

OTHER PUBLICATIONS

Aitken et al., "Role of Active-Site Residues Thr81, Ser82, Thr85, Gln157, and Tyr158 in Yeast Cystathionine β-Synthase Catalysis and Reaction Specificity" *Biochemistry* 43(7):1963-1971, 2004.

Ajith et al., "Homocysteine in ocular diseases," *Clinica Chimica Acta* 450:316-321, 2015.

Alexander et al., "Evolutionary relationships among pyridoxal-5'-phosphate-dependent enzymes. Regio-specific α, β and γ families," *Eur. J. Biochem.* 219: 953-960, 1994.

Allen et al., "Serum betaine, N, N-dimethylglycine and N-methylglycine levels in patients with cobalamin and folate deficiency and related inborn errors of metabolism," *Metabolism* 42(11):1448-1460, Nov. 1993.

Altschul et al., "Basic Local Allignment Search Tool," *J. Mol. Biol.* 215:403-410, 1990.

Altschul et al., "Gapped BLAST and PSI-BLAST: a new generation of protein database search programs," *Nucleic Acids Res.* 25:3389-3402, 1997.

Aoki et al., "Angiogenesis induced by hepatocyte growth factor in non-infarcted myocardium and infarcted myocardium: up-regulation of essential transcription factor for angiogenesis, ets" *Gene Therapy* 7:417-427, 2000.

Australian Examination Report for Australian Application No. 2014212471, dated Feb. 1, 2019.

Banerjee et al., "Redox regulation and reaction mechanism of human cystathionine-β- synthase: a PLP-dependent hemesensor protein," *Archives of Biochemistry and Biophysics* 433:144-156, 2005.

Baranov et al., "Homocystinuria in children*," *Issues of modern pediatrics* 16(6): 457-467, 2017.

Barber et al., "The successful treatment of homocystinuria with pyridoxine." *J. Pediatr.* 75(3):463-78, Sep. 1969.

Bateman, "The structure of a domain common to archaebacteria and the homocystinuria disease protein." *Trends Biochem. Sci.* 22:12-13, Jan. 1997.

Belew et al., "Kinetic characterization of recombinant human cystathionine beta-synthase purified from *E. coli*," *Protein Expression and Purification Academic Press* 64(2):139-145, 2009.

Bennett et al., "Stable transgene expression in rod photoreceptors after recombinant adeno-associated virus-mediated gene transfer to monkey retina" *Proc. Natl. Acad. Sci. USA* 96:9920-9925, Aug. 1999.

Blaese et al., "T Lymphocyte-Directed Gene Therapy for ADA-SCID: Initial Trial Results After 4 Years," *Science* 270:475-480, Oct. 20, 1995.

Bordignon et al., "Gene Therapy in Peripheral Blood Lymphocytes and Bone Marrow for ADA-Immunodeficient Patients," *Science* 270(5235):470-475, Oct. 20, 1995 (7 pages).

Broun et al., "Catalytic Plasticity of Fatty Acid Modification Enzymes Underlying Chemical Diversity of Plant Lipids," *Science* 282:1315-1317, Nov. 13, 1998.

Bruno et al., "Functional Properties of the Active Core of Human Cystathione β-Synthase Crystals," *The Journal of Biological Chemistry* 276(1):16-19, Jan. 5, 2001.

Bublil et al., "Classical homocystinuria: From cystathionine beta-synthase deficiency to novel enzyme therapies," *Biochemie* 173:48-56, 2020.

Bublil et al., "Enzyme replacement with PEGylated cystathionine β-synthase ameliorates homocystinuria in murine model," *J Clin Invest.* 126(6):2372-2384, 2016.

Bukovska et al., "Expression of Human Cystathionine β-Synthase in *Escherichia coli*: Purification and Characterization," *Protein Expression and Purification* 5:442-448, Apr. 1, 1994.

Byrne et al., "DNA Sequences of the cysK Regions of *Salmonella typhimurium* and *Escherichia coli* and Linkage of the cysK Regions to ptsH," *Journal of Bacteriology* 170(7):3150-3157, Jul. 1988.

Carballal et al., "Dioxygen Reactivity and Heme Redox Potential of Truncated Human Cystathionine β-Synthase," *Biochemistry* 47(10): 3194-3201, Feb. 16, 2008.

Carson et al., "Metabolic abnormalities detected in a survey of mentally backward individuals in Northern Ireland." *Arch. Dis. Child* 37(195):505-13, Oct. 1962.

Chassé et al., "Genomic Organization of the Human Cystathionine β-Synthase Gene: Evidence for Various cDNAs," *Biochemical and Biophysical Research Communications* 211(3):826-832, Jun. 26, 1995.

Cherney et al., "Ferrous Human Cystathionine β-Synthase Loses Activity during Enzyme Assay Due to a Ligand Switch Process," *Biochemistry* 46(45): 13199-13210, Oct. 23, 2007.

Clarke et al., "Homocysteine, renal function, and risk of cardiovascular disease," *Kidney International* 63(Supplement 84):S131-S133, 2003.

(56) References Cited

OTHER PUBLICATIONS

ClinicalTrials.gov, "OT-58 as an Enzyme Replacement Therapy for Patients With Cystathionine Beta-Synthase Deficient Homocystinuria (CBSDH)," *U.S. National Library of Medicine*, NCT03406611, first posted Jan. 15, 2018, retrieved Oct. 26, 2022, 9 pages.

ClinicalTrials.gov, "OT-58 as an Enzyme Therapy for Patients with Cystathionine Beta-Synthase Deficient Homocystinuria (CBSDH)," *U.S. National Library of Medicine*, NCT03406611, first posted Dec. 4, 2019, accessed Oct. 26, 2022, 10 pages.

Connolly et al., "Protein Aggregation in Frozen Trehalose Formulations: Effects of Composition, Cooling Rate, and Storage Temperature," *Journal of Pharmaceutical Sciences* 104:4170-4184, Dec. 2015 [Published online Sep. 23, 2015]. (15 pages).

Devos et al., "Practical Limits of Function Prediction," *PROTEINS: Structure, Function, and Genetics* 41:98-107, Jun. 12, 2000.

Ding et al., "Bioconjugated PLGA-4-arm-PEG branched polymeric nanoparticles as novel tumor targeting carriers," *Nanotechnology*: 165101, Apr. 2011. (12 pages).

Dong et al., "Secondary Structure of Recombinant Human Cystathionine β-Synthase in Aqueous Solution: Effect of Ligand Binding and Proteolytic Truncation," *Archives of Biochemistry and Biophysics* 344(1):125-132, Aug. 1, 1997.

D'Souza et al., "Pharmaceutical amyloidosis associated with subcutaneous insulin and enfuvirtide administration." *Amyloid* 21(2):71-75, Jun. 2014. (NIH Public Access Author Manuscript, available in PMC Jun. 1, 2014) (9 pages).

El-Sayed et al., "PLP-Dependent Enzymes: a Potent Therapeutic Approach for Cancer and Cardiovascular diseases," Targets in Gene Therapy, Prof. Yongping You (Ed.), In Tech, pp. 119-146, Aug. 2011.

Examination report No. 2, dated Jun. 14, 2019 for Australian Application No. 2014212471.

Examination Report received in Australian Application No. 2013240003, dated Oct. 5, 2017, 3 pages.

Extended European Search Report for European Application No. 19179948.5 dated Oct. 7, 2019, 9 pages.

Extended European Search Report issued Aug. 7, 2020 in European patent application 20168207.7.

Extended European Search Report received in European Application No. 17165825.5, dated Dec. 4, 2017, 8 pages.

Extended European Search Report received in European Patent Application No. 17172478.4 dated Dec. 11, 2017.

Fee et al., "PEG-proteins: Reaction engineering and separation issues," *Chemical Engineering Science* 61:924-939, 2006.

Fekete et al., "Theory and practice of size exclusion chromatography for the analysis of protein aggregates," *Journal of Pharmaceutical and Biomedical Analysis* 101:161-173, 2014.

Finkelstein et al., "Activation of cystathionine synthase by adenosylmethionine and adenosylethionine," *Biochem. Biophys. Res. Commun.* 66:81-87, 1975.

Finkelstein et al., "Inactivation of Betaine-Homocysteine Methyltransferase by Adenosylmethionine and Adenosylethionine," *Biochemical and Biophysical Research Communications* 118(1):14-19, Jan. 13, 1984.

Finkelstein et al., "Methionine metabolism in mammals. Distribution of homocysteine between competing pathways." *J. Biol. Chem.* 259(15):9508-9513, 1984.

Finkelstein, "Methionine metabolism in mammals." *J. Nutr. Biochem.* 1(5):228-37, May 1990.

First Examination Report for India Application 6010/DELNP/2015, dated Nov. 28, 2019.

Folstein et al., "The Homocysteine Hypothesis of Depression," *Am J Psychiatry* 164:861-867, 2007.

Frank et al., "Purification and characterization of the wild type and truncated human cystathionine β-synthase enzymes expressed in *E. coli*," *Archives of Biochemistry and Biophysics* 470(1):64-72, 2008.

Frank et al., "Solvent-Accessible Cysteines in Human Cystathionine β-Synthase: Crucial Role of Cysteine 431 in S-Adenosyl-L-methionine Binding," *Biochemistry* 45:11021-11029, 2006.

Gallagher et al., "Structure and control of pyridoxal phosphate dependent allosteric threonine deaminase," *Structure* 6(4):465-475, Apr. 15, 1998.

Gaustadnes et al., "Prevalence of Congenital Homocystinuria in Denmark," *N. Engl. J. Med.* 340(19):1513, May 1999.

Green et al., "Molecular Cloning: A Laboratory Manual," Cold Spring Harbor Laboratory Press, Fourth Edition, vol. 1, 2012 (34 pages) (Table of Contents only).

Gupta et al., "Betaine supplementation is less effective than methionine restriction in correcting phenotypes of CBS deficient mice," *J. Inherit. Metab. Dis.* 39:39-46, 2016.

Gupta et al., "Cysthathionine beta-synthase-deficient mice thrive on a low-methionine diet," *FASEB J.* 28(2):781-90, Feb. 2014.

Gupta et al., "Mouse models of cystathionine beta-synthase deficiency reveal significant threshold effects of hyperhomocysteinemia." *FASEB J.* 23(3):883-893, Mar. 2009.

Halperin et al., "The Influences of Environmental Enrichment, Cognitive Enhancement, and Physical Exercise on Brain Development: Can we Alter the Developmental Trajectory of ADHD?" *Neurosci Biobehav Rev.* 35(3):621-634, Jan. 2011 (NIH Public Access Author Manuscript, available in PMC Jan. 1, 2012) (31 pages).

Harris et al., "Effect of pegylation on pharmaceuticals," *Nature Reviews Drug Discovery* 2(3):214-221, Mar. 2003.

Henikoff et al., "Amino acid substitution matrices from protein blocks," *Proc. Natl. Acad. Sci. USA* 89:10915-10919, Nov. 1992. (5 pages).

Huang et al., "Liposomal gene delivery: A complex package," *Nature Biotechnology* 15:620-621, Jul. 1997.

Indian Examination Report for Indian Application No. 7920/DELNP/2014 dated Jan. 29, 2019. (6 pages) (with English Translation).

International Preliminary Report on Patentability, dated Oct. 1, 2014, for International Application No. PCT/US2013/033716. (7 pages).

International Search Report and Written Opinion, dated Jan. 23, 2017, for International Patent Application No. PCT/US2016/061050.

International Search Report, dated Jun. 21, 2013, for International Application No. PCT/US2013/033716. (5 pages).

International Search Report, mailed Jun. 17, 2014, for International Application No. PCT/US2014/013602. (6 pages).

Izutsu et al., "Freeze-drying of protein pharmaceuticals," *Pharmacology* 72(6):353-358, 2012 (with Machine Translation). (12 pages).

Izutsu et al., "Characterization of Frozen Aqueous Solution for Formulation and Process Design of Freeze-dried Pharmaceuticals," *Netsu Sokutei* 36(2):112-120, 2009 (with English abstract). (9 pages).

Jakubowski et al., "Mutations in cystathionine β-synthase or methylenetetrahydrofolate reductase gene increase N-homocysteinylated protein levels in humans," *FASEB J* 22(12):4071-4076, 2008.

James et al., "Metabolic biomarkers of increased oxidative stress and impaired methylation capacity in children with autism," *Am J Clin Nutr* 80:1611-1617, Dec. 2004. (7 pages).

Janoïk et al., "Crystallization and preliminary X-ray diffraction analysis of the active core of human recombinant cystathione β-synthase: an enzyme involved in vascular disease," *Acta Crystallogr. D Biol. Crystallogr.* 57(Pt 2):289-291, 2001.

Janoïk et al., "Impaired Heme Binding and Aggregation of Mutant Cystathionine β-Synthase Subunits in Homocystinuria," *Am. J. Hum. Genet.* 68(6):1506-1513, May 15, 2001.

Janoïk et al., "Regulation of Human Cystathionine β-synthase by S-Adenosyl-L-methionine: Evidence for Two Catalytically Active Conformations Involving an Autoinhibitory Domain in the C-terminal Region," *Biochemistry* 40(35):10625-10633, 2001.

Jhee et al., "Domain Architecture of the Heme-Independent Yeast Cystathionine β-synthase Provides Insights into Mechanisms of Catalysis and Regulation," *Biochemistry* 39(34):10548-10556, 2000.

Jhee et al., "Forum Review: The Role of Cystathionine β-Synthase in Homocysteine Metabolism," *Antioxid. Redox Signal.* 7(5-6):813-822, 2005.

(56) References Cited

OTHER PUBLICATIONS

Jhee et al., "Yeast Cystathionine β-Synthase Is a Pyridoxal Phosphate Enzyme but, Unlike the Human Enzyme, Is Not a Heme Protein." *The Journal of Biological Chemistry* 275(16):11541-11544, Apr. 21, 2000.

Jinping et al., "Advance in Cystathionine beta-Synthase Research," *Med. J. West China* 18(5):657-659, Sep. 2006 (7 pages) (with English Translation).

Kabil et al., "Deletion of the Regulatory Domain in the Pyridoxal Phosphate-dependent Heme Protein Cystathionine β-Synthase Alleviates the Defect Observed in a Catalytic Site Mutant," *The Journal of Biological Chemistry*, 274(44):31256-31260, Oct. 29, 1999.

Kaneda et al., "Prevention of Restenosis by Gene Therapy," *Annals New York Academy of Sciences*, 299-310, 1997.

Kang et al., "Emerging PEGylated drugs," *Expert opinion on emerging drugs* 14(2):363-380, Jun. 2009.

Kery et al., "Binding of Pyridoxal 5'-Phosphate to the Heme Protein Human Cystathionine β-Synthase," *Biochemistry* 38(9):2716-2724, Feb. 9, 1999.

Kery et al., "Transsulfuration Depends on Heme in Addition to Pyridoxal 5'-Phosphate. Cystathionine β-Synthase is a Heme Protein," *The Journal of Biological Chemistry* 269(41):25283-25288, Oct. 14, 1994.

Kery et al., "Trypsin Cleavage of Human Cystathionine β-Synthase into an Evolutionarily Conserved Active Core: Structural and Functional Consequences," *Arch. Biochem. Biophys.* 355(2):222-232, Jul. 1998.

Kery et al., "δ-Aminolevulinate Increases Heme Saturation and Yield of Human Cystathionine β-Synthase Expressed in *Escherichia coli*," *Archives of Biochemistry and Biophysics* 316(1):24-29, Jan. 10, 1995.

Kim et al., "Functional modeling of vitamin responsiveness in yeast: a common pyridoxine-responsive cystathionine β-synthase mutation in homocystinuria," *Human Mol. Genet.* 6(13):2213-2221, 1997.

Kitano, "Biological robustness." *Nature Reviews Genetics* 5(11):826-837, Nov. 2004.

Kluijtmans et al., "Defective Cystathionine β-Synthase Regulation by S-Adenosylmethionine in a Partially Pyridoxine Responsive Homocystinuria Patient," *J. Clin. Invest.* 98(2):285-289, Jul. 1996.

Knudson et al., "Evaluating Separations of PEGylated Proteins Using Gel Filtration Chromatography," Phenomenex, Inc., Dec. 2008 (4 pages).

Koeberl et al., "Persistent expression of human clotting factor IX from mouse liver after intravenous injection of adeno-associated virus vectors," *Proc. Natl. Acad. Sci. USA* 94:1426-1431, Feb. 1997.

Komrower et al., "Dietary Treatment of Homocystinuria." *Arch. Dis. Child* 41(220):666-671, Dec. 1966.

Kožich et al., "Screening for Mutations by Expressing Patient cDNA Segments in *E. coli*: Homocystinuria due to Cystathionine β-Synthase Deficiency," Hum. Mutation 1:113-123, 1992.

Kraus et al., "Cystathionine β-Synthase and Its Deficiency." In Carmel et al. (eds.), *Homocysteine in Health and Disease*, Cambridge University Press, Cambridge, United Kingdom, pp. 223-243, 2001.

Kraus et al., "Cystathionine β-synthase from Human Liver: Improved Purification Scheme and Additional Characterization of the Enzyme in Crude and Pure Form," *Arch. Biochem. Biophys.* 222(1):44-52, Apr. 1983.

Kraus et al., "Human cystathionine β-synthase cDNA: sequence, alternative splicing and expression in cultured cells," *Human Molecular Genetics* 2(10):1633-1638, 1993.

Kraus et al., "Purification and Properties of Cystathionine β-Synthase from Human Liver," *J. Biol. Chem.* 253(18):6523-6528, 1978.

Kraus, "Cystathionine β-synthase (human)," *Methods Enzymol.* 143:388-394, 1987.

Kruger et al., "A yeast system for expression of human cystathionine β-synthase: Structural and functional conservation of the human and yeast genes," *Proc. Natl. Acad. Sci. USA* 91:6614-6618, Jul. 1994.

Kutzbach et al., "Feedback inhibition of methylene-tetrahydrofolate reductase in rat liver by S-adenosylmethionine," *Biochim. Biophys. Acta* 139:217-220, 1967.

Kutzbach et al., "Mammalian Methylenetetrahydrofolate Reductase. Partial Purification, Properties, and Inhibition by S-Adenosylmethionine," *Biochim. Biophys. Acta* 250:459-477, 1971.

Levine et al., "Adenoviral-Mediated Gene Transfer to Human Adipocytes In Vitro, and Human Adipose Tissue Ex Vivo and Rabbit Femoral Adipose Tissue In Vivo," *J Nutr. Sci. Vitaminol.* 44:569-572, 1998.

Levy, "Physician's Guide to The Homocystinurias," *National Organization for Rare Disorders (NORD)*, Jan. 2010, Retrieved from Internet: URL:http://www.rarediseases.org/docs/Homocystinuria_11_29b.pdf (8 pages).

Li et al., "Homocystinuria and Phychiatric Disorder: A Case Report," *Pathology* 31(3):221-224, 1999.

Linnebank et al., "High Prevalence of the 1278T Mutation of the Human Cystathionine β-Synthase Detected by a Novel Screening Application," *Thromb. Haemost.* 85(6):986-988, Jun. 2001.

Linnebank et al., "Isolated thrombosis due to the cystathionine β-synthase mutation c.833T>C (1278T)," *J. Inherited Metabol. Dis.* 26(5):509-511, Jun. 2003.

Lodha et al., "Investigation of residues Lys112, Glu136, His138, Gly247, Tyr248, and Asp249 in the active site of yeast cystathionine β-synthase," *Biochem. Cell Biol.* 87:531-540, 2009.

Lowry et al., "Protein Measurement With the Folin Phenol Reagent." *J. Biol. Chem.* 193(1):265-275, 1951.

Lu et al., "Hcy promotes the formation of atherosclerotic and effect of liver lipid metabolism disorder in ApoE-/- mice," *Chongqing Medicine* (30):4030-4033, 2014. (with English Abstract).

MacLean et al., "A novel trangenic mouse model of CBS-deficient homocystinuria does not incur hepatic steatosis or fibrosis and exhibits a hypercoagulative phenotype that is ameliorated by betaine treatment," *Mol. Genet. Metab.* 101:153-162, Oct.-Nov. 2010.

MacLean et al., "Cystathionine beta-synthase null homocystinuric mice fail to exhibit altered hemostasis or lowering of plasma homocysteine in response to betaine treatment," *Mol. Genet. Metab.* 101:163-171, Oct.-Nov. 2010.

MacLean et al., "Cystathionine Protects against Endoplasmic Reticulum Stress-induced Lipid Accumulation, Tissue Injury, and Apoptotic Cell Death," *J. Biol. Chem.* 287(38):31994-32005, Sep. 14, 2012.

Maclean et al., "High Homocysteine and Thrombosis Without Connective Tissue Disorders Are Associated With a Novel Class of Cystathionine β-Synthase (CBS) Mutations," *Hum. Mutat.* 19:641-655, 2002.

Maclean et al., "Transsulfuration in *Saccharomyces cerevisiae* is not dependent on heme: purification and characterization of recombinant yeast cystathionine β-synthase." *Journal of Inorganic Biochemistry* 81:161-171, 2000.

Majtan et al., "Behavior, body composition, and vascular phenotype of homocystinuric mice on methionine-restricted diet or enzyme replacement therapy," *FASEB J.* 33:12477-12486, Nov. 2019.

Majtan et al., "Engineering and Characterization of an Enzyme Replacement Therapy for Classical Homocystinuria," *Biomacromolecules* 18:1747-1761, Apr. 21, 2017.

Majtan et al., "Enzyme replacement prevents neonatal death, liver damage, and osteoporosis in murine homocystinuria," *FASEB J.* 31:5495-5506, Dec. 2017.

Majtan et al., "Enzyme Replacement Therapy Ameliorates Multiple Symptoms of Murine Homocystinuria," *Molecular Therapy* 26(3):834-844, Mar. 2018.

Majtan et al., "Folding and activity of mutant cystathionine β-synthase depends on the position and nature of the purification tag: characterization of the R266K CBS mutant." *Protein Expr. Purif.* 82(2):317-324, 2012 (NIH Public Access Author Manuscript, available in PMC Apr. 1, 2013) (21 pages).

Majtan et al., "Interplay of enzyme replacement therapy, diet and betaine in murine cystathionine beta-synthase-deficient homo cystinuria," *J Inherit Metab Dis* 41(Suppl 1):S56, 2018. (2 pages).

Majtan et al., "Pharmacokinetics and pharmacodynamics of PEGylated truncated human cystathionine beta-synthase for treatment of homocystinuria," *Life Sciences* 200:15-25, 2018.

(56) References Cited

OTHER PUBLICATIONS

Majtan et al., "Purification and characterization of cystathionine β-synthase bearing a cobalt protoporphyrin," *Archives of Biochemistry and Biophysics* 508:25-30, 2011.

Majtan et al., "Rescue of Cystathionine β-Synthase (CBS) Mutants with Chemical Chaperones: Purification and Characterization of Eight CBS Mutant Enzymes." *J Biol Chem.* 285(21):15866-15873, May 21, 2010.

Mansoor et al., "Determination of the in Vivo Redox Status of Cysteine, Cysteinylglycine, Homocysteine, and Glutathione in Human Plasma," *Analytical Biochemistry* 200:218-229, 1992.

Mansoor et al., "Redox status and protein binding of plasma homocysteine and other aminothiols in patients with early-onset peripheral vascular disease, homocysteine and peripheral vascular disease." *Arterioscler Thromb Vasc Biol*, 15(2):232-240, Feb. 1995.

Mansoor et al., "Redox status and protein binding of plasma homocysteine and other aminothiols in patients with homocystinuria," *Metabolism* 42(11):1481-1485, Nov. 1993, 1 page (Abstract only).

Maurice et al., "Enhancement of cardiac function after adenoviral-mediated in vivo intracoronary β2-adrenergic receptor gene delivery," *J Clin. Invest.* 104(1):21-29, Jul. 1999.

Maurice et al., "Enhancement of cardiac function after adenoviral-mediated in vivo intracoronary β2-adrenergic receptor gene delivery," *J Clin. Invest.* 104:21-29, Jul. 1999.

Meier et al., "Structure of human cystathionine β-synthase: a unique pyridoxal 5'-phosphate-dependent heme protein," *EMBO J.* 20(15):3910-3916, 2001.

Melenovská et al., "Chaperone therapy for homocystinuria: the rescue of CBS mutations by heme arginate." *J. Inherit. Metab. Dis.* 38(2); 284-297, Mar. 2015.

Miles et al., "Cystathionine β-synthase: structure, function, regulation, and location of homocystinuria-causing mutations." *J. Biol. Chem.* 279(29):29871-29874, 2004.

Millecamps et al., "Neuron-restrictive silencer elements mediate neuron specificity of adenoviral gene expression," *Nature Biotechnology* 17:865-869, Sep. 1999.

Mudd et al., "Disorders of transsulfuration, " in Stanbury et al. (eds.), *The Metabolic and Molecular Bases of Inherited Disease*, 8 Ed., McGraw-Hill, New York , pp. 2007-2056, 2001.

Mudd et al., "Homocysteine and its disulfide derivatives: A suggested consensus terminology," *Arterioscler. Thromb. Vasc. Biol.* 20:1704-1706, Jul. 2000.

Mudd et al., "Homocystinuria: An enzymatic defect." *Science* 143(3613):1443-1445, Mar. 1964.

Mudd et al., "The natural history of homocystinuria due to cystathionine β-synthase deficiency," Am. J. Hum. Genet. 37(1):1-31, Jan. 1985.

Münke et al., "The gene for cystathionine β-synthase (CBS) maps to the subtelomeric region on human chromosome 21q and to proximal mouse chromosome 17," *Am. J. Hum. Genet.* 42(4):550-559, Apr. 1988.

Needleman et al., "A general method applicable to the search for similarities in the amino acid sequence of two proteins," *J. Mol. Biol.* 48(3):443-453, Mar. 1970.

Nozaki et al., "Characterization of Transsulfuration and Cysteine Biosynthetic Pathways in the Protozoan Hemoflagellate, *Trypanosoma cruzi*. Isolation and Molecular Characterization of Cystathionine β-Synthase and Serine Acetyltransferase from *Trypanosoma*," *The Journal of Biological Chemistry* 276(9):6516-6523, Mar. 2, 2001.

Office Action, dated Apr. 18, 2018, for Japanese Application No. 2015555429. (with English Translation).

Office Action, dated Apr. 26, 2018, for Chinese Application No. 201480006554.0. (with English Translation).

Office Action, dated Aug. 21, 2017, for Israel Application No. 234635. (3 pages) (with English Translation).

Office Action, dated Jan. 9, 2019, for Canadian Application No. 2867719.

Office Action, dated Jun. 14, 2019, for Japanese Application No. 2017-078808. (with English Translation) (13 pages).

Office Action, dated Jun. 2, 2020, for Japanese Application No. 2018232350.

Office Action, dated Jun. 24, 2018, for Israel Application No. 239783.

Office Action, dated Mar. 25, 2019, for Israel Application No. 263162. (3 pages).

Office Action, dated May 21, 2018, for Israel Application No. 234635. (3 pages) (with English Translation).

Office Action, dated May 3, 2017, for Chinese Application No. 201380027463.0. (with English Translation).

Office Action, dated Nov. 6, 2019, for Japanese Application No. 2018232350.

Office Action, dated Oct. 12, 2020, for Chinese Application No. 2016800762750.

Office Action, dated Oct. 13, 2020, for Brazil Application No. BR112018007768-2.

Office Action, dated Oct. 18, 2019, for Canadian Application 2,898,772.

Office Action, dated Oct. 23, 2020, for Japanese Application No. 2019-187777. (11 pages) (with English translation).

Office Action, dated Oct. 25, 2018, for Japanese Application No. 2017-078808. (13 pages) (with English Translation).

Office Action, dated Sep. 11, 2020, for Japanese Application No. 2017-078808. (3 pages) (with English Translation).

Office Action, dated Sep. 22, 2017, for Japanese Application No. 2015-555429. (19 pages) (with English Translation).

Office Action, dated Sep. 29, 2020, for Japanese Application No. 2018-523444.

Office Action, mailed Feb. 27, 2018, for Japanese Application No. 2017-078808. (10 pages) (with English Translation).

Ojha et al., "Effects of Heme Ligand Mutations Including a Pathogenic Variant, H65R, onthe Properties of Human Cystathionine β-Synthase," *Biochemistry* 41(14):4649-4654, 2002.

Oligino et al., "Intra-articular delivery of a herpes simplex virus IL-1Ra gene vector reduces inflammation in a rabbit model of arthritis," *Gene Therapy* 6:1713-1720, Jun. 16, 1999.

Ono et al., "Purification and Properties of *Saccharomyces cerevisiae* Cystathionine β- Synthase," *Yeast* 10:333-339, 1994.

O'Shannessy et al., "Determination of Rate and Equilibrium Binding Constants for Macromolecular Interactions Using Surface Plasmon Resonance: Use of Nonlinear Least Squares Analysis Methods," *Analytical Biochemistry* 212:457-468, 1993.

Park et al., "Hypermethioninemia Leads to Fatal Bleeding and Increased Mortality in a Transgenic 1278T Mouse Model of Homocystinuria," *Biomedicines* 8:244, Jul. 24, 2020. (15 pages).

Park et al., "Interplay of Enzyme Therapy and Dietary Management of Murine Homocystinuria," *Nutrients* 12:2895, Sep. 22, 2020. (13 pages).

Park et al., "Long-term uninterrupted enzyme replacement therapy prevents liver disease in murine model of severe homocystinuria," *Human Mutation* 41:1662-1670, Jul. 2, 2020.

Park et al., "Recombinant adeno-associated virus mediated gene transfer in a mouse model for homocystinuria," *Exp. Mol. Med.* 38(6):652-661, Dec. 2006.

Pasut et al., "Pegylation for improving the effectiveness of therapeutic biomolecules," *Drugs of Today* 45(9):687-695, 2009.

Pasut et al., "State of the art in PEGylation: The great versatility achieved after forty years of research," *Journal of Controlled Release* 161(2):461-472, 2012.

Pearson et al., "Improved tools for biological sequence comparison," *Proc. Nat'l. Acad. Sci. USA* 85(8):2444-2448, Apr. 1988.

Pfister et al., "Process for protein PEGylation," *Journal of Controlled Release* 180:134-149, 2014.

Preliminary Office Action, dated Jun. 10, 2020, for Brazil Patent Application No. BR112014023570-8.

Refsum et al., "Facts and recommendations about total homocysteine determinations: an expert opinion," Clin. Chem. 50:3-32, Jan. 2004.

Régnier et al., "Brain Phenotype of Transgenic Mice Overexpressing Cystathionine β-Synthase," *PLOS One* 7(1):e29056 (10 pages).

Reslan et al., "Lack of a synergistic effect of arginine-glutamic acid on the physical stability of spray-dried bovine serum albumin," *Pharmaceutical Development and Technology* 22(6):785-791, 2017 [Published online May 19, 2016]. (8 pages).

(56) References Cited

OTHER PUBLICATIONS

Robert et al., "Cystathionine β Synthase Deficiency Promotes Oxidative Stress, Fibrosis, and Steatosis in Mice Liver," *Gastroenterology* 128:1405-1415, 2005.

Robichon et al., "Engineering *Escherichia coli* BL21(DE3) Derivative Strains To Minimize *E. coli* Protein Contamination after Purification by Immobilized Metal Affinity Chromatography," *Applied and Environmental Microbiology* 77(13):4634-4646, Jul. 2011.

Rolland et al., "O-Acetylserine(thiol)lyase from Spinach (*Spinacia oleracea* L.) Leaf: cDNA Cloning, Characterization, and Overexpression in *Escherichia coli* of the Chloroplast Isoform," *Archives of Biochemistry and Biophysics* 300(1):213-222, Jan. 1993.

Roper et al., "Rat cystathionine β-synthase: expression of four alternatively spliced isoforms in transfected cultured cells." *Arch. Biochem. Biophys.* 298(2):514-521, 1992.

Sacharow et al., "Homocystinuria Caused by Cystathionine Beta-Synthase Deficiency," *GeneReviews*:1-21, Jan. 15, 2004.

Saluta et al., "Troubleshooting GST fusion protein expression in *E. coli*," *Life Science News* 1: 1-3, 1998.

Salzmann et al., "Rates of Evolution of Pyridoxal-5'-Phosphate-Dependent Enzymes," *Biochemical and Biophysical Research Communications* 270(2):576-580, 2000.

Schiff et al., "Treatment of Inherited Homocystinurias," *Neuropediatrics* 43:295-304, 2012 (10 Pages).

Schuster et al., "Assembly and function of a quaternary signal transduction complex monitored by surface plasmon resonance," *Nature* 365:343-347, Sep. 23, 1993.

Seffernick et al., "Melamine Deaminase and Atrazine Chlorohydrolase: 98 Percent Identical but Functionally Different, " *J. Bacteriol.* 183(8):2405-2410, Apr. 2001.

Sen et al., "Cystathionine-β-synthase gene transfer and 3-deazaadenosine ameliorate inflammatory response in endothelial cells," *Am J Physiol Cell Physiol* 293: C1779-C1787, Sep. 13, 2007.

Shan et al., "Correction of disease-causing CBS mutation in yeast," *Nature Genetics* 19:91-93, May 1998.

Shan et al., "Mutations in the regulatory domain of cystathionine β-synthase can functionally suppress patient-derived mutations in cis," *Human Molecular Genetics* 10(6):635-643, 2001.

Singh et al., "Functional Rescue of Mutant Human Cystathionine β-Synthase by Manipulation of Hsp26 and Hsp70 Levels in *Saccharomyces cerevisiae*," *The Journal of Biological Chemistry* 284(7):4238-4245, Feb. 13, 2009.

Singh et al., "Modulation of the Heme Electronic Structure and Cystathionine β-synthase Activity by Second Coordination Sphere Ligands: The Role of Heme Ligand Switching in Redox Regulation," *J Inorg Biochem* 103(5):689-697, May 2009 (NIH Public Access Author Manuscript, available in PMC May 1, 2010) (23 pages).

Skovby et al., "Assignment of the genes for cystathionine β-synthase to human chromosome 21 in somatic cell hybrids," *Hum. Genet.* 65(3):291-294, Apr. 1984.

Smith et al., "Comparison of biosequences," *Adv. Appl. Math.* 2(4):482-489, Dec. 1981.

Sokolova et al., "Cystathionine beta-synthase deficiency in Central Europe: discrepancy between biochemical and molecular genetic screening for homocystinuric alleles," *Hum. Mutat* 18(6):548-549, Dec. 2001.

Stabler et al., "Elevated plasma total homocysteine in severe methionine adenosyltranferase I/III deficiency," *Metabolism* 51(8):981-988, Aug. 2002.

Stribling et al., "Aerosol gene delivery in vivo," *Proc. Natl. Acad. Sci. USA* 89:11277-11281, Dec. 1992.

Tan et al., "Polyethylene Glycol Conjugation of Recombinant Methionase for Cancer Therapy, " *Protein Expression and Purification* 12:45-52, Feb. 1998.

Taoka et al., "Assignment of Enzymatic Functions to Specific Regions of the PLP-Dependent Heme Protein Cystathionine β-Synthase," *Biochemistry* 38(40):13155-13161, 1999.

Taoka et al., "Characterization of NO binding to human cystathionine β-synthase: Possible implications of the effects of CO and NO binding to the human enzyme," *Journal of Inorganic Biochemistry* 87:245-251, 2001.

Taoka et al., "Characterization of the Heme and Pyridoxal Phosphate Cofactors of Human Cystathionine β-Synthase Reveals Nonequivalent Active Sites," *Biochemistry* 38:2738-2744, Feb. 5, 1999.

Taoka et al., "Evidence for Heme-mediated Redox Regulation of Human Cystathionine β-Synthase Activity," *The Journal of Biological Chemistry* 273(39):25179-25184, Sep. 25, 1998.

Taoka et al., "Stopped-flow Kinetic Analysis of the Reaction Catalyzed by the Full-Length Yeast Cystathionine β-Synthase," *The Journal of Biological Chemistry* 277(25):22421-22425, Jun. 21, 2002.

Van Guldener et al., "Homocysteine-lowering treatment: an overview," *Expert Opin Pharmacother.* 2(9): 1449-1460, 2001.

Van Guldener, "Why is homocysteine elevated in renal failure and what can be expected from homocysteine-lowering?" *Nephrol Dial Transplant* 21:1161-1166, 2006.

Van Meurs et al., "Homocysteine Levels and the Risk of Osteoporotic Fracture," *N Engl J Med* 350(20):2033-2041, May 13, 2004.

Vargas et al., "Detection of c-type cytochromes using enhanced chemiluminescence." *Anal. Biochem.* 209(2):323-326, 1993.

Volpe et al., "Transsulfuration in fetal and postnatal mammalian liver and brain. Cysthathionine synthase, its relation to hormonal influences and cystathionine," *Biol. Neonate* 20(5):385-403, 1972.

Von der Leyen et al., "Gene therapy inhibiting neointimal vascular lesion: In vivo transfer of endothelial cell nitric oxide synthase gene," *Proc. Natl. Acad. Sci. USA* 92:1137-1141, Feb. 1995.

Vozdek et al., "Novel structural arrangement of nematode cystathionine β- synthases:characterization of Caenorhabditis elegans CBS-1," *Biochem. J.* 443:535-547, 2012.

Vugmeyster et al., "Pharmacokinetics and toxicology of therapeutic proteins: Advances and challenges," *World Journal of Biological Chemistry* 3(4):73-92, Apr. 2012.

Walter et al., "Strategies for the treatment of cystathionine β-synthase deficiency: the experience of the Willink Biochemical Genetics Unit over the past 30 years," *Eur. J. Pediatr.* 157(Suppl 2):S71-6, Apr. 1998.

Wang et al., "Expression of mutant human cystathionine β-synthase rescues neonatal lethality but not homocystinuria in a mouse model," *Human Molecular Genetics* 14(15):2201-2208, Jun. 22, 2005.

Wang et al., "Expression, Purification and Characterization of Recombinant Human CBS in *Escherichia coli*," *Progress in Modern Biomedicine* 11(5):830-833, Mar. 2011 (with English Abstract).

Watanabe et al., "Mice deficient in cysthathionine β-synthase: animal models for mild and severe homocyst(e)inemia," *Proc. Natl. Acad. Sci. U.S.A.* 92(5):1585-1589, Feb. 1995.

Whisstock et al., "Prediction of protein function from protein sequence and structure," *Quarterly Reviews of Biophysics* 36(3):307-340, 2003.

Wilcken et al., "Homocystinuria-the effects of betaine in the treatment of patients not responsive to pyridoxine," *N. Engl. J. Med.* 309(8):448-453, 1983.

Witkowski et al., "Conversion of a β-Ketoacyl Synthase to a Malonyl Decarboxylase by Replacement of the Active-Site Cysteine with Glutamine," *Biochemistry* 38:11643-11650, Aug. 1999.

Yamanishi et al., "Structural insights into pathogenic mutations in heme-dependent cystathionine-β-synthase," *Journal of Inorganic Biochemistry* 100:1988-1995, Sep. 20, 2006.

Yap et al., "The intellectual abilities of early-treated individuals with pyridoxine-nonresponsive homocystinuria due to cystathionine β-synthase deficiency," *J. Inherit. Metab. Dis.* 24:437-447, 2001.

Yap et al., "Vascular outcome in patients with homocystinuria due to cystathionine beta-synthase deficiency treated chronically: a Multicenter observational study," *Arterioscler. Thromb. Vasc. Biol.* 21(12):2080-2085, Dec. 2001.

Yap, "Classical homocystinuria: Vascular risk and its prevention," *J. Inherit. Metab. Dis.* 26:259-265, 2003.

(56) References Cited

OTHER PUBLICATIONS

Yap, "Homocystinuria due to cystathionine β-synthase deficiency," *Orphanet Encyclopedia*, Feb. 2005, Retrieved from Internet: URL: http://www.orpha.net/data/patho/GB/uk-CbS.pdf (13 Pages).

Zhang et al., "Characteristics and Crystal Structure of Bacterial Inosine-5'-monophosphate Dehydrogenase," *Biochemistry* 38(15):4691-4700, Mar. 26, 1999.

Zou et al., "Tumor Necrosis Factor-α-induced Targeted Proteolysis of Cystathionine β-Synthase Modulates Redox Homeostasis," *The Journal of Biological Chemistry* 278(19):16802-16808, May 9, 2003.

Bonadio, "Macaca fascicularis: long-tailed macaque," Animal Diversity Web, University of Michigan Museum of Zoology, 2000, retrieved from URL=https://animaldiversity.org/accounts/Macaca_fascicularis/, on Jul. 22, 2025. (9 pages).

Stabler et al., "Metabolic Profiling of Total Homocysteine and Related Compounds in Hyperhomocysteinemia: Utility and Limitations in Diagnosing the Cause of Puzzling Thrombophilia in a Family," JIMD Reports 11:149-163, Jun. 4, 2013. (15 pages).

Non-PEGylated htCBS

PEGhtCBS (GL4-400MA)

COMPOSITIONS AND METHODS FOR TREATMENT OF HOMOCYSTINURIA

REFERENCE AN ELECTRONIC SEQUENCE LISTING

The present application is being filed along with a Sequence Listing in electronic format. The contents of the electronic sequence listing (431C6_SeqListing.xml; Size: 28,245 bytes; and Date of Creation: May 8, 2024) is herein incorporated by reference in its entirety.

FIELD OF THE INVENTION

The present invention generally relates to enzyme replacement therapy (ERT) using human Cystathionine Beta-Synthase (CBS), or a modified version thereof (e.g., human truncated CBS (htCBS) or a variant thereof), to significantly reduce serum homocysteine (Hcy) concentrations, and restore levels of its downstream metabolites such as cystathionine and cysteine. Further, ERT with CBS, htCBS or a modified version thereof can be used for treatment of diseases such as homocystinuria and homocysteine remethylation disorders.

BACKGROUND OF THE INVENTION

Cystathionine beta-synthase (CBS) is the first enzyme in the transsulfuration pathway, catalyzing the condensation of serine and homocysteine (Hcy) to cystathionine, which is then hydrolyzed to cysteine by Cystathionine Gamma Lyase (CGL). In systems biology, robustness of a biological system is defined as its ability to function properly in face of perturbations, and redundancy of elements in the system is one of the mechanisms by which such robustness is achieved (Kitano, H. 2004, Nature Reviews Genetics, 5:826-837). However, the biological transsulfuration system seems to largely lack redundancy of components, making this system prone to mutational perturbations. For example, the CBS enzyme is the only component that can process homocysteine to cystathionine. A limited system redundancy partly exists as homocysteine, the first metabolite that funnels into the pathway, can alternatively be converted to methionine through the remethylation pathway, thus relieving the homocysteine load. In addition, cysteine, a downstream product, can be obtained directly from diet. Nevertheless, these pathways are limited in their capacity to maintain normal levels of metabolites, and lack of CBS function has detrimental consequences for human patients if left untreated. Inactivation of CBS results in cystathionine beta-synthase-deficient homocystinuria (CBSDH), more commonly referred to as classical homocystinuria.

There exist limited therapeutic options to treat CBSDH and current treatment options reduce homocysteine but do not tend to normalize cystathionine (Cth) or cysteine (Cys) and thus these treatment options may be inadequate for providing robust and effective treatment options. Thus, there remains a need in the art for more effective treatment strategies for individuals with homocystinuria.

The present invention addresses this need by providing compositions and methods of using these compositions for the treatment of CBSDH.

SUMMARY OF THE INVENTION

The present disclosure provides compositions suitable for enzyme replacement therapy comprising human truncated cystathionine beta synthase (htCBS) and variants thereof which may also be PEGylated. The htCBS composition may be used to reduce homocysteine levels and raise levels of downstream metabolites cystathionine and cysteine, may be used to treat conditions and diseases such as homocystinuria (e.g., CBSDH) and homocysteine remethylation disorders and they also may be used to improve liver pathology.

Provided herein are methods for treating homocystinuria in a subject by administering to a subject a composition comprising an htCBS or htCBS mutant polypeptide. The htCBS or htCBS mutant polypeptide may be PEGylated with a low molecular weight or high molecular weight PEG. The htCBS or htCBS mutant polypeptide may be administered at a dose between 5 and 7.5 mg/kg and may be administered at least twice a week. Further, the htCBS or htCBS mutant polypeptide may be co-administered with betaine, or other known CBSDH therapies.

Provided herein are methods for increasing the amount of a metabolite such as, but not limited to, cystathionine and cysteine, in a subject by administering to a subject a composition comprising an htCBS or htCBS mutant polypeptide. The htCBS or htCBS mutant polypeptide may be PEGylated with a low molecular weight or high molecular weight PEG. The htCBS or htCBS mutant polypeptide may be administered at a dose between 5 and 7.5 mg/kg and may be administered at least twice a week. Further, the htCBS or htCBS mutant polypeptide may be co-administered with betaine. The amount of cystathionine may be increased to 0.005-0.35 uM. The amount of cysteine may be increased to above 140 uM (e.g., between 200 uM to 400 uM)

Provided herein are methods for decreasing the amount of a metabolite such as, but not limited to, homocysteine, methionine S-adenosyl homocysteine, and S-adenosyl methionine in a subject by administering to a subject a composition comprising an htCBS or htCBS mutant polypeptide. The htCBS or htCBS mutant polypeptide may be PEGylated with a low molecular weight or high molecular weight PEG. The htCBS or htCBS mutant polypeptide may be administered at a dose between 5 and 7.5 mg/kg and may be administered at least twice a week. Further, the htCBS or htCBS mutant polypeptide may be co-administered with betaine. The amount of homocysteine may be decreased to less than 100 uM (e.g., about 10 uM). The amount of methionine may be decreased to less than 50 uM (e.g., about 30 uM). The amount of S-adenosyl homocysteine may be decreased to less than 0.14 uM (e.g., about 0.015 uM)

Provided herein are methods for treating liver disease in a subject by administering to a subject a composition comprising an htCBS or htCBS mutant polypeptide. The htCBS or htCBS mutant polypeptide may be PEGylated with a low molecular weight or high molecular weight PEG. The htCBS or htCBS mutant polypeptide may be administered at a dose between 5 and 7.5 mg/kg and may be administered at least twice a week.

Additional embodiments of the present compositions and methods, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

BRIEF DESCRIPTION OF THE DRAWINGS

FIG. 1A shows enzyme retention time in plasma is maintained suggesting that rapid loss of activity in vivo is a result of clearance. FIG. 1B shows enzyme retention time is in vivo is enhanced for PEGylated htCBS and that PEGylation does not influence specific activity of the enzyme. Mouse #1 and Mouse #2 in FIG. 1B are also described as FIG. 1B in International Patent Publication No. WO2014120770, the contents of which are herein incorporated by reference in its entirety.

FIG. 5A is also described as FIG. 5A in International Patent Publication No. WO2014120770, the contents of which are herein incorporated by reference in its entirety. FIG. 5B is also described as FIG. 5B in International Patent Publication No. WO2014120770, the contents of which are herein incorporated by reference in its entirety. FIG. 5C is also described as FIG. 5C in International Patent Publication No. WO2014120770, the contents of which are herein incorporated by reference in its entirety. FIG. 5F is also described as FIG. 6A in International Patent Publication No. WO2014120770, the contents of which are herein incorporated by reference in its entirety. FIG. 5G is also described as part of FIG. 7A and FIG. 7B in International Patent Publication No. WO2014120770, the contents of which are herein incorporated by reference in its entirety. FIG. 5H is also described as FIG. 6C in International Patent Publication No. WO2014120770, the contents of which are herein incorporated by reference in its entirety.

DETAILED DESCRIPTION

Figure 1A:
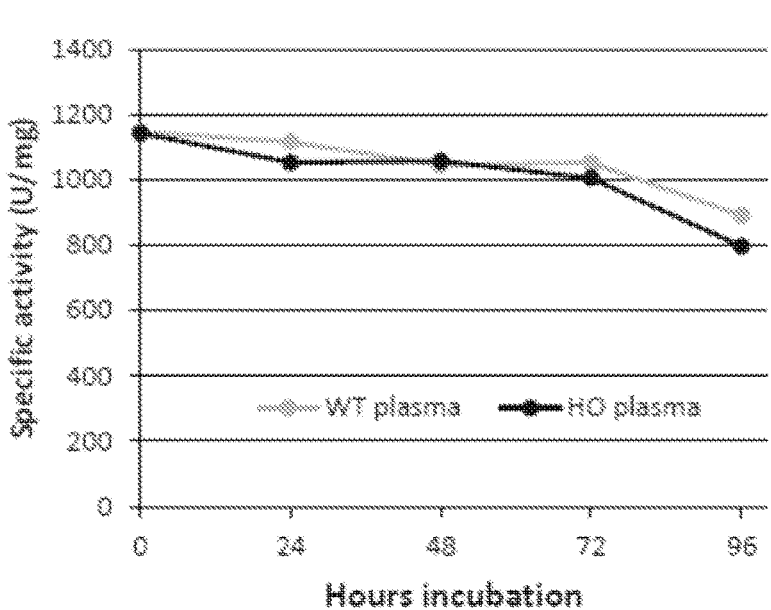
FIG. 1A-1B show enzyme retention in plasma and in vivo.

Provided herein are compositions and methods for treating cystathionine beta-synthase-deficient homocystinuria (CBSDH). As a non-limiting example, CBSDH may be treated by enzyme replacement of CBS or a variant thereof.

Inactivation of CBS results in cystathionine beta-synthase-deficient homocystinuria (CBSDH), more commonly referred to as classical homocystinuria. CBSDH is an autosomal recessive disorder characterized by markedly elevated plasma total homocysteine (tHcy) and methionine levels, and greatly reduced concentrations of cystathionine and cysteine; it is the most common sulfur-amino acid defect. If untreated, CBSDH results in diseases, disorders and/or conditions in a variety of different organ systems and severe phenotypic changes. Non-limiting examples of diseases, disorders and/or conditions from CBSDH include mental retardation, psychiatric disturbances, central nervous system problems including seizures, cardiovascular disease with a predisposition to thromboembolic complications resulting in a high rate of mortality in untreated and partially treated individuals, and a range of connective tissue disorders affecting the ocular system (e.g., progressive myopia and lens dislocation, ectopia lentis), and skeletal system (e.g., marfanoid habitus, osteoporosis, scoliosis, fine fair hair and brittle, thin skin).

There is a functional trichotomy in the nature of pathogenic mutations associated with CBSDH. One group of mutations is classified as "pyridoxine-responsive," where CBS enzyme function may be partially restored by high dose Vitamin B6 therapy. This treatment can be effective, but does not always mitigate the pathological events in these individuals, and some of the events occur even in these individuals over time. In a clinical setting "Vitamin $B_6$ responsive" is defined as a 30% relative drop in Hcy that occurs 24 hours after an individual is given an oral dose of 100-500 mg of B6, meaning that a B6 responsive individual may still have abnormally high homocysteine levels. The second group of functional mutations is represented by the "C-terminal CBS mutants" that are defective in their ability to respond to post-translational up-regulation by S-adenosylmethionine. Individuals with this class of mutations usually lack the mental retardation and connective tissue aspects of the phenotype. This class is detected after measurement of plasma Hcy levels following an idiopathic thrombotic event before the age of 40 years (Maclean et al., 2002, *Hum. Mutat.* 19:641-55). The final group of CBSDH mutations is "classical homocystinuria," which represents the most severe form of the disease. For these latter two groups of individuals Vitamin $B_6$ therapy in isolation does not effectively lower serum Hcy levels. These mutational groups may show phenotypic distinctions, but can be treated similarly.

The most common mutated CBS allele is 833T>C (I278T), which is associated with pyridoxine-responsive homocystinuria. Thus, $B_6$ responsive individuals account for approximately half of the homocystinuric patient population (Barber and Spaeth, 1969; Mudd et al., 1985). Of these $B_6$ responsive individuals, however, many are only partial responders, and in combination with $B_6$ non-responsive individuals, there arises a need for additional therapeutic options. Unfortunately, such therapeutic options are currently limited to reducing intake of methionine by following a strict low protein diet with supplemented cysteine (now essential) and decreasing homocysteine concentration via the use of betaine (N,N,N-trimethylglycine), a methyl donor able to re-methylate homocysteine back to methionine. Therefore, enzyme replacement therapy (ERT) using CBS (e.g., PEGylated htCBS described herein) may be the best therapy for both the $B_6$ partial and non-responsive patients.

As a result of CBS dysfunction, homocysteine (Hcy) levels are dramatically altered in CBSDH patients. In healthy individuals, total Hcy levels are in the range of ~5-15 μM (Stabler et al., 2002, *Metabolism,* 51:981-988), 98% of which is in the form of disulfides or is protein-bound. Only 2% of the tHcy exists as a free (non-protein-bound) reduced homocysteine, which can serve as a substrate for CBS (Mansoor et al., 1992, *Anal. Biochem.* 200:218-229;

Mudd et al., 2000, *Arterioscler. Thromb. Vasc. Biol.* 20:1704-1706). This balance is dramatically altered in CBSDH patients, with free reduced homocysteine reaching 10-25% of tHcy values that are observed in these patients (up to ~400 µM) (Mansoor et al., 1993, *Metabolism,* 42:1481-1485).

Higher tHcv levels (e.g., greater than 54 times the wild type levels) may also cause diseases, disorders and/or conditions such as, but not limited to, facial alopecia, osteoporosis and reduction in mean survival. As a non-limiting example, model mice having at least 54 times higher tHcy as compared to wild type demonstrated several diseases, disorders and/or conditions, including facial alopecia, osteoporosis and reduction in mean survival. However, no such signs were observed in mice which had tHcy levels of about 30 times the normal values and thus homocysteine elevation may only pathogenic only above a threshold level (Gupta et al., 2009, *FASEB J.* 23:883-893). In a multicenter observational study of CBSDH in humans, it was found that even though various treatment combinations failed to restore normal homocysteine levels in CBSDH patients, and B₆ non-responders continued to exhibit homocysteine levels 3-5 times higher than the upper limit in the normal population, the risk of thromboembolism in these patients was significantly reduced (Yap et al., 2001, *Arterioscler. Thromb. Vasc. Biol.* 21, 2080-2085). Collectively, these data indicate that in order to ameliorate the clinical manifestation of CBSDH, an incomplete reduction of tHcy, as long as it is below a threshold level, may be sufficient to treat disease.

While a low methionine diet can be effective in establishing and maintaining some metabolic control of homocysteine levels in patients, its effect may be hindered by lack of dietary compliance especially in late-diagnosed patients, resulting in a concomitant increase in homocysteine accompanied by development of symptoms, especially in children (Walter et al., 1998, *Eur. J. Pediatr.* 157 Suppl 2, S71-76). Failure of dietary compliance causes increased serum Hcy, resurgence of complications in the vascular and connective tissue including fatal and incapacitating events, and risk of severe side-effects such as cerebral edema (from excessive serum Met concentration) or severe malnutrition (from lack of essential amino acids). The most effective therapeutic strategy is to increase enzyme activity, as is evident when given pyridoxine to Vitamin B₆ responsive homocystinuria. This strategy is not possible for Vitamin B₆ non-responsive individuals due to the mutation status. Betaine may help to achieve a metabolic control in less compliant patients and its combination with the diet may represent the best available treatment. However, current therapies for B₆ non-responders do not increase cystathionine, and cysteine supplementation may be warranted in order to maintain proper levels. Increased enzyme activity in these individuals may therefore depend on the delivery of exogenous enzyme, i.e. enzyme replacement therapy (ERT).

Considerable evidence suggests a possible function for cystathionine independent of its role as an intermediate in transsulfuration. A positive role for cystathionine has been suggested by studies of a particular transgenic mouse model of CBS-deficient homocystinuria. In this model of classical homocystinuria, the mouse cbs gene is inactivated and survives on low-level expression of the human CBS transgene under the control of the human CBS promoter; thus, it has been designated as "human only" (HO). The HO mouse exhibits severe elevations in both plasma and tissue levels of Hcy, methionine, S-adenosylmethionine, and S-adenosylhomocysteine and a concomitant decrease in plasma and hepatic levels of cysteine. However, in contrast to previous CBS knockout models of classical homocystinuria (also known as CBS knockout mice (KO) which suffer a severe growth retardation and hepatopathy and most die within three weeks after birth, even while mothers are on betaine (Maclean et al., 2010b. *Mol. Genet. Metab.* 101, 153-162)), which suffer severe growth retardation and hepatopathy, incur hepatic steatosis, fibrosis, and neonatal death within three weeks after birth even while mothers are treated with betaine, the HO mice exhibit mild hepatopathy and approximately 90% of HO mice live for at least 6 months (Maclean et al., 2012, J. Biol. Chem. 287, 31994-32005, the contents of which are herein incorporated by reference in its entirety). Tail bleeding determinations indicate that HO mice are in a hypercoagulative state that is significantly ameliorated by betaine treatment in a manner that recapitulates the disease as it occurs in humans (Maclean et al., 2010b. Mol. Genet. Metab. 101, 153-162; the contents of which are herein incorporated by reference in its entirety). HO mice have high levels of tHcy, but suffer only minor consequences. There is little or no difference in metabolite levels between these two murine models, except the level of cystathionine, which is significantly elevated in HO mice (~10 µM) as compared to KOs (~1 µM). Thus, it has been suggested that cystathionine may exert protective effects against hepatic and renal lipid accumulation, tissue injury and apoptotic cell death induced by prolonged endoplasmic reticulum stress.

Cystathionine may exert protective effects in a mouse model of acetaminophen-induced liver injury by serving as a cysteine prodrug. The use of the CGL inactivating compound D,1-2-amino-4-pentynoic acid in experiments to induce hypercystathionemia by blocking the conversion of cystathionine to cysteine coupled with the observation that cystathionine exerts significant protective effects in a23 cells that are incapable of converting this compound to cysteine, indicate that the protective effects observed are not a result of cystathionine acting as a precursor for cysteine synthesis.

Cystathionine may be important to the normally functioning brain. It is possible that cystathionine specifically accumulates in the normal mammalian brain to serve as a cytoprotectant and that the abolition of its synthesis could contribute to mental retardation in homocystinuria by increasing sensitivity of neural tissues to the toxic insult of elevated Hcy and/or derivatives thereof (Maclean et al., 2012, J. Biol. Chem. 287, 31994-32005). There are considerable regional differences in concentrations of cystathionine within the brain, and there is a higher concentration in white matter than in grey matter, suggesting a possible role in myelination. Cystathionine has been found in higher levels in occipital lobes of human and monkey brains than in the whole brain of lower animal species, and the role of cystathionine has been suggested to be more important in primate than in rodent brain (Volpe and Laster, 1972, *Biol. Neonate* 20, 385-403; the contents of which are herein incorporated by reference in its entirety).

A number of indirect lines of evidence support possible physiological roles for either cystathionine or a derivative thereof. In primate brain and central nervous system (CNS), there appears to be an imbalance between the relative activity levels of CBS and CGL leading to an accumulation of cystathionine. Similarly, during embryonic development, CBS is expressed in multiple tissues such as the heart and lungs that do not express any detectable CBS in adult tissues. A range of data indicates that CGL is not expressed during early mammalian development. In human liver samples for instance, CGL activity is only detected in post-natal tissue whereas activity in fetal, premature and full-term neonatal liver tissue is essentially undetectable.

Collectively, these results indicate that at certain stages of development and in adult neural tissues, CBS is expressed specifically for the production of cystathionine distinct from its role as an intermediate in cysteine synthesis (Maclean et al., 2012, *J. Biol. Chem.* 287, 31994-32005; the contents of which are herein incorporated by reference in its entirety). Taken with the knowledge that rigorous control over cystathionine γ-lyase (CGL) and CBS expression occurs during mammalian development, these observations come together to suggest a possible protective role for cystathionine in addition to being a precursor to cysteine.

Cysteine biosynthesis from cystathionine is catalyzed by CGL. Cystathionine is present inside the cells, and it is believed to not exist as a plasma protein. Accordingly, it is believed that the cystathionine produced upon injection of the PEGylated human truncated (htCBS) enzyme described herein may also serve as an intracellular substrate for CGL. Additionally, it may be possible that reduced levels of tHcy may impede the formation of cysteine-homocysteine adducts (which can be rapidly cleared in urine), generating higher levels of free cysteine in plasma (Gupta et al., 2014, *FASEB J.* 28:781-790).

Various aspects of the present invention now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

The CBS Enzyme

The CBS gene resides on human chromosome 21 at q22.3 (Skovby et al., *Hum. Genet.* 65:291-294 (1984); Munke et al., *Am. J. Hum. Genet.* 42:550-559 (1988); the contents of which are herein incorporated by reference in their entirety). The nucleic acid sequence encoding human CBS and the amino acid sequence encoded thereby are available through GenBank Accession No. L19501, and these sequences are also disclosed in U.S. Pat. No. 5,523,225, which is incorporated herein by reference in its entirety. The nucleic acid sequence of the genomic DNA encoding CBS is also publicly available through sequence databases such as GenBank and at University of Colorado-Denver webpage (Kraus Laboratory).

While not wishing to be bound by theory, the protein encoded by the CBS gene acts as a homotetramer to catalyze the conversion of homocysteine to cystathionine, the first step in the transsulfuration pathway. The encoded protein is allosterically activated by S-adenosyl-methionine and uses pyridoxal phosphate as a cofactor. Multiple alternatively spliced transcript variants have been found for this gene.

CBS governs the unidirectional flow of sulfur from methionine to cysteine by operating at the intersection of the transmethylation, transsulfuration and re-methylation pathways. It catalyzes a β-replacement reaction in which serine condenses with homocysteine in a pyridoxal 5'-phosphate (PLP)-dependent manner, to form cystathionine (Miles and Kraus, 2004, *J. Biol. Chem.* 279:29871-29874; the contents of which are herein incorporated by reference in its entirety). Cystathionine can then be converted to cysteine by Cystathionine Gamma Lyase (CGL). Thus, proper function of the CBS enzyme is critical for the regulation of both cysteine and methionine metabolism (Mudd et al., 2001, "Disorders of Transsulfuration." In The Metabolic and molecular bases of inherited disease. C. R. Scriver, A. L. Beudet, W. S. Sly, V. D., C. B., K. K. W., and V. B., eds. (New York:

McGraw-Hill), pp. 2007-2056; the contents of which are herein incorporated by reference in its entirety), and accordingly, a compromised CBS activity or lack thereof, leads to the biochemical and clinical manifestations of CBS-deficient homocystinuria (CBSDH).

Inactivation of CBS results in cystathionine beta-synthase-deficient homocystinuria (CBSDH), more commonly referred to as classical homocystinuria. Classical homocystinuria was first described by Carson and Neill in 1962 (Carson and Neill, 1962. *Arch. Dis. Child* 37:505-513; the contents of which are herein incorporated by reference in its entirety) and is recognized as the most common inborn error of sulfur amino acid metabolism. The underlying cause of homocystinuria, a deficiency of the Cystathionine β-Synthase (CBS) enzyme, was discovered shortly thereafter (Mudd et al., 1964, *Science* 143:1443-1445; the contents of which are herein incorporated by reference in its entirety).

Missense mutations represent the most common cause of cystathionine β-synthase (CBS) deficiency. Many of these mutations result in misfolded proteins, which lack biological function. The presence of chemical chaperones (e.g., such as ethanol, dimethyl sulfoxide, or trimethylamine-N-oxide) can sometimes alleviate or even restore protein folding and activity of mutant proteins. Eight CBS mutant enzymes (P49L, P78R, A114V, R125Q, E176K, P422L, I435T, and S466L) were purified and characterized, and could be rescued with chemical chaperones by improving their protein folding. The tetrameric mutant enzymes fully saturated with heme had the same or higher specific activities than wild type CBS. Thermal stability measurements demonstrated that the purified mutants are equally or more thermostable than wild type CBS. The response to S-adenosyl-L-methionine stimulation or thermal activation varied. The lack of response of R125Q and E176K to both stimuli indicated that their specific conformations were unable to reach the activated state. Increased levels of molecular chaperones in crude extracts, particularly DnaJ, indicated a rather indirect effect of the chemical chaperones on folding of CBS mutants (Majtan, et al., 2010, *J. Biol. Chem.* 285 (21): 15866-15873; the contents of which are herein incorporated by reference in its entirety).

The extent of misfolding of 27 CBS mutations previously tested in *E. coli* have been tested for the ability of chaperones to rescue the conformation of these mutations under the more folding-permissive conditions of mammalian CHO-K1 cells. Expression of mutations in mammalian cells increased the median activity 16-fold and the amount of tetramers 3.2-fold compared with expression in bacteria. Subsequently, the responses of seven selected mutations to three compounds with chaperone-like activity were tested. Aminooxyacetic acid and 4-phenylbutyric acid exhibited only a weak effect. In contrast, heme arginate substantially increased the formation of mutant CBS protein tetramers (up to sixfold) and rescued catalytic activity (up to ninefold) of five out of seven mutations (p.A114V, p.K102N, p.R125Q, p.R266K, and p.R369C). The greatest effect of heme arginate was observed for the mutation p.R125Q, which is non-responsive to in vivo treatment with vitamin B6. Moreover, the heme responsiveness of the p.R125Q mutation was confirmed in fibroblasts derived from a patient homozygous for this genetic variant. Based on these data, a distinct group of heme-responsive CBS mutations was proposed and the heme pocket of CBS was predicted to be an important target for designing novel therapies for homocystinuria (Melenovska, et al., 2014, *J. Inherit. Metab. Dis.* 38 (2); the contents of which are herein incorporated by reference in its entirety).

Biochemically, CBSDH is characterized by highly elevated blood levels of homocysteine, methionine and S-adenosyl-homocysteine (also known as "SAH" or "AdoHcy"), accompanied by low levels of cysteine and cystathionine. Some of the clinical manifestations of untreated homocystinuria include thromboembolism, connective tissue problems such as dislocation of the optic lens, marfanoid features and osteoporosis, cognitive impairment and other signs (Kraus, J., and Kozich, V. (2001). "Cystathionine beta-synthase and its deficiency." In Homocysteine in health and disease. J. D. Carmel R, ed. (New York: Cambridge University Press), pp. 223-243; Mudd et al., 2001, "Disorders of Transsulfuration." In The Metabolic and molecular bases of inherited disease. C. R. Scriver, A. L. Beudet, W. S. Sly, V. D., C. B., K. K. W., and V. B., eds. (New York: McGraw-Hill), pp. 2007-2056).

Initial attempts to treat homocystinuria employed dietary restrictions to decrease the methionine intake, thus avoiding the build-up of the toxic homocysteine (Komrower et al., 1966, *Arch. Dis. Child* 41:666-671). It was later found that supplementation with the PLP-cofactor precursor, pyridoxine (vitamin B$_6$), relieves the clinical manifestations for slightly less than half of patients, and a subset of these are only partial responders (Barber and Spaeth, 1969. *J. Pediatr.* 75:463-478; Mudd et al., 1985, *Am. J. Hum. Genet.* 37:1-31). The "B$_6$ responders" need to take supplemental vitamin B$_6$ for the rest of their lives. In many cases, even full B$_6$-responsive patients require a milder protein restricted diet to be able to achieve a metabolic control (Picker, J. D., and Levy, H. L. (2004). Homocystinuria Caused by Cystathionine Beta-Synthase Deficiency. In Gene Reviews. R. A. Pagon, M. P. Adam, T. D. Bird, C. R. Dolan, C. T. Fong, and K. Stephens, eds. (Seattle (WA): University of Washington, Seattle; the contents of each of which are herein incorporated by reference in their entirety). The remaining subset, the non-responders, are subjected to an extremely limited diet, with which many patients poorly comply (Walter et al., 1998, Eur. J. Pediatr. 157 Suppl 2, S71-76; the contents of which are herein incorporated by reference in its entiery). The diet is combined with a methionine-free and cysteine enriched amino acid mixture along with betaine, which can serve as a methyl donor for the enzyme betaine-homocysteine methyltransferase (BHMT) to produce dimethylglycine and methionine from homocysteine (Finkelstein, 1990, *J. Nutr. Biochem.* 1:228-237). Glutathione is synthesized from cysteine, and thus the addition of cysteine can be important to reduce oxidative stress. Most patients are also treated with trimethylglycine, and a normal dose of folic acid supplement. This improves the metabolic control by lowering homocysteine levels, in conjunction with the strict diet.

Betaine (N,N,N-trimethylglycine) is used to reduce concentrations of homocysteine by promoting the conversion of homocysteine back to methionine, i.e., increasing flux through the remethylation pathway independent of folate derivatives (which is mainly active in the liver and in the kidneys). A small portion of the re-formed methionine is then gradually removed by incorporation into body protein. The methionine that is not converted into protein is converted to S-adenosyl-methionine which goes on to form homocysteine again. Betaine is, therefore, most effective if the quantity of methionine to be removed is small. Hence treatment includes both betaine and a diet low in methionine. In classical homocystinuria, the plasma methionine level usually increases above the normal range of 30 micromoles/L and the concentrations should be monitored as potentially toxic levels (more than 400 micromoles/L) may be reached.

An alternative treatment strategy for CBSDH has long been sought to provide the B$_6$ non-responders and partial responders with a therapy that improves the metabolic abnormalities, reduces the accumulation of toxic homocysteine in circulation, and increases the levels of cystathionine and cysteine. Such metabolic changes may reverse, or delay, the onset of CBSDH symptoms, and allow this group of affected individuals to enjoy an unrestricted or only mildly restricted diet and significantly improve their quality of life. To provide these benefits, a therapy must improve the core deficiency that underlies this condition, namely, aberrant CBS levels and/or function. Accordingly, systemic introduction of CBS, in the form of Enzyme Replacement Therapy (ERT), should be beneficial for homocystinuric patients.

Without being bound by theory, a significant decrease in extracellular homocysteine due to CBS administration is believed to generate a concentration gradient, triggering a flux of homocysteine from intra- to extra-cellular spaces, where the administered enzyme can further process it, and thus the extracellular CBS can serve as a homocysteine "sink."

The structure and mode of activation of native human CBS, which exists as a tetramer, comprised of four identical monomers may be difficult to use as ERT. This form of the enzyme has a high tendency for aggregation, which poses a major constraint on the purification efforts (Kraus and Rosenberg, 1983, *Arch. Biochem. Biophys.* 222:44-52; the contents of which are herein incorporated by reference in its entirety). Additionally, CBS activation requires the binding of S-Adenosyl-methionine (SAM) to the C-terminal tail, in order to relieve the auto-inhibition exerted on the enzyme by its C-terminal regulatory region.

A truncated recombinant human CBS (htCBS) is provided (SEQ ID NO: 3) where the C-terminal regulatory region has been removed. In one embodiment, the htCBS may be mutated where cysteine at amino acid position 15 has been changed to serine (htCBS mutant or C15S) (SEQ ID NO: 13).

In one embodiment, PEGylated htCBS or PEGylated htCBS mutant enzyme improved the pharmacokinetic and pharmacodynamic properties of the enzyme in vivo. Therapeutic proteins, unlike small molecules, are delivered via parenteral routes, and treatment efficacy may be greatly impacted by their absorption, distribution, metabolism and excretion ("ADME") (Vugmeyster et al., 2012, *World Journal of Biological Chemistry* 3:73-92; the contents of which are herein incorporated by reference in its entirety). High molecular weight compounds, such as enzymes, have limited tissue penetration capability, and are thus mainly present in the plasma until they are removed from circulation by at least one mechanism.

In one embodiment, administration of htCBS or htCBS mutant for ERT maintains high activity in plasma for a period of time that is sufficient to deliver a steady and significant effect on sulfur amino acid metabolism. Enhancing ERT efficacy may require additional modifications to the protein, in order to increase retention time in vivo. This may be achieved by PEGylation, the addition of Poly-Ethylene-Glycol (PEG) moieties onto the surface of the protein, in order to extend the retention time in a subject. PEGylation was found to minimize proteolysis, immune response and antigenicity, while increasing protein stability and size, and reducing renal excretion (Kang et al., 2009, *Expert opinion*

*on emerging drugs* 14:363-380; the contents of which are herein incorporated by reference in its entirety).

Cysteine biosynthesis from cystathionine is catalyzed solely by CGL. Cystathionine is only present inside the cells, and does not exist as a plasma protein. Accordingly, it is believed that the cystathionine produced upon injection of the PEGylated htCBS or PEGylated htCBS mutant enzyme described herein may also serve as an intracellular substrate for CGL. Additionally, and not mutually exclusively, it is also possible that reduced levels of tHcy may impede the formation of cysteine-homocysteine adducts (which can be rapidly cleared in urine), generating higher levels of free cysteine in plasma, as was recently suggested (Gupta et al., 2014, *FASEB J.* 28, 781-790). Normalizing cysteine levels without cysteine supplementation is another potential advantage of the presently described htCBS and htCBS mutant in ERT.

In one embodiment, normalization of cysteine levels may be observed following administration of the PEGylated htCBS or PEGylated htCBS mutant enzyme. In addition to a change in metabolite levels, another positive effect of htCBS or htCBS mutant administration may be predicted to be a significant impact on liver disease and survival of affected CBSDH patients.

Methods of Using PEGylated htCBS

In one embodiment, the compositions and methods described herein may be used to treat CBSDH. There are three groups of pathogenic mutations associated with CBSDH, (1) pyridoxine-responsive mutations, (2) C-terminal CBS mutants and (3) classical homocystinuria.

In one embodiment, htCBS and htCBS mutant enzyme replacement may be used to treat CBSDH. The htCBS and htCBS mutant enzyme may be PEGylated by a method known in the art or described herein. As a non-limiting example, the PEG may be a low molecular weight (e.g., 2 kDa) PEG or a high molecular weight (e.g., 40 kDa) four arm branched PEG.

In one embodiment, PEGylated htCBS or PEGylated htCBS mutant and methods of using the PEGylated htCBS or PEGylated htCBS mutant described herein may be used to treat subjects with pyridoxine-responsive mutations. PEGylated htCBS or PEGylated htCBS mutant may be used alone or in combination with current therapies (e.g., Vitamin B6 or Betaine) to treat subjects with pyridoxine-responsive mutations. As a non-limiting example, the PEGylated htCBS or PEGylated htCBS mutant may be used to mitigate or reduce pathological events in subjects with pyridoxine-responsive mutations. As a non-limiting example, the PEGylated htCBS or PEGylated htCBS mutant may be used to treat a subject with pyridoxine-responsive mutations who is a partial responder to Vitamin B6 therapy. As another non-limiting example, the PEGylated htCBS or PEGylated htCBS mutant may be used to treat a subject with pyridoxine-responsive mutations who is a non-responder to Vitamin B6 therapy.

In one embodiment, PEGylated htCBS or PEGylated htCBS mutant and methods of using the PEGylated htCBS or PEGylated htCBS mutant described herein may be used to treat subjects with C-terminal CBS mutations. PEGylated htCBS or PEGylated htCBS mutant may be used alone or in combination with current therapies (e.g., Vitamin B6 or Betaine) to treat subjects with C-terminal CBS mutations. As a non-limiting example, the PEGylated htCBS or PEGylated htCBS mutant may be used to lower serum Hcy levels in subjects with C-terminal CBS mutations. As a non-limiting example, the PEGylated htCBS or PEGylated htCBS mutant may be used to treat a subject with C-terminal CBS mutations who is a partial responder to Vitamin B6 therapy. As another non-limiting example, the PEGylated htCBS or PEGylated htCBS mutant may be used to treat a subject with C-terminal CBS mutations who is a non-responder to Vitamin B6 therapy.

In one embodiment, PEGylated htCBS or PEGylated htCBS mutant and methods of using the PEGylated htCBS or PEGylated htCBS mutant described herein may be used to treat subjects with classical homocystinuria. PEGylated htCBS or PEGylated htCBS mutant may be used alone or in combination with current therapies (e.g., Vitamin B6 or Betaine) to treat subjects with classical homocystinuria. As a non-limiting example, the PEGylated htCBS or PEGylated htCBS mutant may be used to lower serum Hcy levels in subjects with classical homocystinuria. As a non-limiting example, the PEGylated htCBS or PEGylated htCBS mutant may be used to treat a subject with classical homocystinuria who is a partial responder to Vitamin B6 therapy. As another non-limiting example, the PEGylated htCBS or PEGylated htCBS mutant may be used to treat a subject with classical homocystinuria who is a non-responder to Vitamin B6 therapy.

In one embodiment, the compositions and methods described herein may be used to reduce a symptom, disease or disorder associated with CBSDH. The symptom, disease or disorder may be in an organ system or a severe phenotypic change. Non-limiting examples of diseases, disorders and/or conditions from CBSDH include mental retardation, psychiatric disturbances, central nervous system problems including seizures, cardiovascular disease with a predisposition to thromboembolic complications resulting in a high rate of mortality in untreated and partially treated individuals, and a range of connective tissue disorders affecting the ocular system (e.g., progressive myopia and lens dislocation, ectopia lentis), and skeletal system (e.g., marfanoid habitus, osteoporosis, scoliosis, fine fair hair and brittle, thin skin).

In one embodiment, the compositions and methods described herein may be used to treat a disease, disorder and/or condition such as, but not limited to, thromboembolism, connective tissue problems such as dislocation of the optic lens, marfanoid features, osteoporosis, and cognitive impairment.

In one embodiment, the PEGylated htCBS or PEGylated htCBS mutant enzyme described herein may reduce the effects and/or treat liver disease. The liver disease may be in a subject with CBSDH. The treatment and/or reduction of the effects of liver disease may thus increase the rate of survival of CBSDH patients. As a non-limiting example, PEGylated htCBS or PEGylated htCBS mutant may be used to reduce liver parenchyma damage.

In one embodiment, PEGylated htCBS or PEGylated htCBS mutant may be used to increase cystathionine and treat or reduce the effects of liver disease or injury.

In one embodiment, the compositions and methods described herein (e.g., enzyme replacement therapy (ERT)) using the PEGylated htCBS or PEGylated htCBS mutant enzyme can ameliorate the disease manifestations and metabolic abnormalities that characterize the homocystinuria.

In one embodiment, ERT using PEGylated htCBS or PEGylated htCBS mutant enzyme offers an effective therapy for CBSDH patients to allow prevention and treatment of and/or amelioration of symptoms of homocystinuria, and relieving the need to maintain such a strict protein-excluding diet.

In one embodiment, PEGylated htCBS or PEGylated htCBS mutant may be used to increase cystathionine and treat or reduce the effects of mental retardation in homocystinuria subjects. The amount of cystathionine may be increased in a region or area of the brain such as, but not limited to, occipital lobes grey matter and white matter.

In one embodiment, PEGylated htCBS or PEGylated htCBS mutant may be used to increase sensitivity of neural tissues in the brain of homocystinuria subjects. The amount of cystathionine may be increased in a region or area of the brain such as, but not limited to, occipital lobes grey matter and white matter.

In one embodiment, PEGylated htCBS or PEGylated htCBS mutant may be used to extend the life of a subject with CBSDH.

In one embodiment, PEGylated htCBS or PEGylated htCBS mutant is used as part of CBS enzyme replacement therapy (ERT) for the treatment of homocystinuria. The administration of PEGylated htCBS and htCBS mutant may not necessitate introduction of the deficient enzyme into its natural intracellular compartment.

In one embodiment, administration of PEGylated htCBS or PEGylated htCBS mutant decrease homocysteine levels by 5%, 10%, 15%, 20%, 25%, 30%, 33%, 35%, 40%, 45%, 50%, 52% 55%, 60%, 65%, 67%, 69%, 70%, 74%, 75%, 76%, 77%, 80%, 85%, 90%, 95% or more than 95%. As a non-limiting example, the decrease of homocysteine may be a decrease of about 69%. As a non-limiting example, the decrease of homocysteine may be a decrease of about 67%. As a non-limiting example, the decrease of homocysteine may be a decrease of about 52%. As a non-limiting example, the decrease of homocysteine may be a decrease of about 33%.

In one embodiment, PEGylated htCBS or PEGylated htCBS mutant may be administered before, after or concurrently with traditional betaine treatment. The combination therapy may result in synergistic effects on homocysteine levels.

In one embodiment, administration of PEGylated htCBS or PEGylated htCBS mutant to a subject may alter the extra- and intra-cellular equilibrium of sulfur amino acids.

In one embodiment, the alteration of extra- and intra-cellular equilibrium may be a decrease in the plasma homocysteine such as, but not limited to, a decrease of about 5%, 10%, 15%, 20%, 25%, 30%, 33%, 35%, 40%, 45%, 50%, 52% 55%, 60%, 65%, 67%, 69%, 70%, 74%, 75%, 76%, 77%, 80%, 85%, 90%, 95% or more than 95%. As a non-limiting example, the decrease of plasma homocysteine may be a decrease of about 75%.

In one embodiment, the alteration of extra- and intra-cellular equilibrium may be an increase in cystathionine such as, but not limited to, an increase of about 10%, 20%, 30%, 40%, 50%, 60%, 70%, 80%, 90%, 100%, 110%, 1120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 460%, 470%, 480%, 490%, 500%, 510%, 520%, 530%, 540%, 550%, 560%, 570%, 580%, 590%, 600%, 610%, 620%, 630%, 640%, 650%, 660%, 670%, 680%, 690%, 700%, 710%, 720%, 730%, 740%, 750%, 760%, 770%, 780%, 790%, 800%, 810%, 820%, 830%, 840%, 850%, 860%, 870%, 880%, 890%, 900%, 910%, 920%, 930%, 940%, 950%, 960%, 970%, 980%, 990%, 1000% or more than 1000%. As a non-limiting example, increase in cystathionine may be about 900%.

In one embodiment, the alteration of extra- and intra-cellular equilibrium may be the normalization of cysteine concentrations that is reflected in improvement of his-topathological changes in the liver and increased survival.

In one embodiment, PEGylated htCBS or PEGylated htCBS mutant may be used to reduce tHcv levels in a subject with CBSDH. The tHCV levels may be reduced to 1, 2, 3, 4, 5, 6, 7, 8, 9, 10, 11, 12, 13, 14, 15, 16, 17, 18, 19, 20 21, 22, 23, 24, 15, 26, 27, 28, 29, 30, 31, 32, 33, 34, 35, 36, 37, 38, 39, 40, 41, 42, 43, 44, 45, 46, 47, 48, 49, 50, 51, 52, 53, 54, 1-5, 1-10, 1-20, 1-30, 1-40, 1-50, 2-5, 2-10, 2-20, 2-30, 2-40, 2-50, 3-5, 3-10, 3-20, 3-30, 3-40, 3-50, 4-6, 4-10, 4-20, 4-30, 4-40, 4-50, 5-7, 5-10, 5-20, 5-30, 5-40, 5-50, 6-8, 6-10, 6-20, 6-30, 6-40, 6-50, 7-10, 7-20, 7-30, 7-40, 7-50, 8-10, 8-20, 8-30, 8-40, 8-50, 9-10, 9-20, 9-30, 9-40, 9-50, 10-20, 10-30, 10-40, 10-50, 20-30, 20-40, 20-50, 30-40, 30-50 or 40-50 times the wild type level. As a non-limiting example, the tHCY level is reduced to about 30 times the wild type level. As a non-limiting example, the tHCY level is reduced to about 3-5 times the wild type level.

In one embodiment PEGylated htCBS or PEGylated htCBS mutant may be used to lower tHcv levels and thus treat or reduce the effects of diseases, disorders and/or conditions associated with high tHCY levels (e.g., greater than 54 times the wild type level). Non-limiting examples, of diseases, disorder and/or conditions associated with high tHCY levels include facial alopecia, osteoporosis and reduction in mean survival.

In one embodiment, the PEGylated htCBS or PEGylated htCBS mutant described herein may be used to normalizing cysteine levels without cysteine supplementation.

In one embodiment, the PEGylated htCBS or PEGylated htCBS mutant described herein may be used in combination with Betaine to reduce concentrations of homocysteine in a subject. Homocysteine may be reduced about 5%, 10%, 15%, 20%, 25%, 30%, 33%, 35%, 40%, 45%, 50%, 52% 55%, 60%, 65%, 67%, 69%, 70%, 74%, 75%, 76%, 77%, 80%, 85%, 90%, 95% or more than 95% in a subject using the combination therapy. As a non-limiting example, homo-cysteine may be reduced 77%. As a non-limiting example, homocysteine may be reduced 76%. As a non-limiting example, homocysteine may be reduced 74%. As a non-limiting example, homocysteine may be reduced 40%.

In one embodiment, the PEGylated htCBS or PEGylated htCBS mutant described herein may be used to cause a change such as an increase and/or decrease in metabolite levels.

In one embodiment, the PEGylated htCBS or PEGylated htCBS mutant described herein may be used to cause a change such as an increase in metabolite levels. As a non-limiting example, the metabolite may be cystathionine and cysteine which may be increased 5%, 10%, 15%, 20%, 25%, 30%, 33%, 35%, 40%, 45%, 50%, 52% 55%, 60%, 65%, 67%, 69%, 70%, 74%, 75%, 76%, 77%, 80%, 85%, 90%, 95%, 100%, 110%, 1120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 460%, 470%, 480%, 490%, 500%, 510%, 520%, 530%, 540%, 550%, 560%, 570%, 580%, 590%, 600%, 610%, 620%, 630%, 640%, 650%, 660%, 670%, 680%, 690%, 700%, 710%, 720%, 730%, 740%, 750%, 760%, 770%, 780%, 790%, 800%, 810%, 820%, 830%, 840%, 850%, 860%, 870%, 880%, 890%, 900%, 910%, 920%, 930%, 940%, 950%, 960%, 970%, 980%, 990%, 1000% or more than 1000%. As a non-limiting example, the amount of cystathionine may be increased to be above 0.008, 0.01, 0.015, 0.020, 0.025, 0.03, 0.035, 0.04, 0.045, 0.05, 0.055, 0.06, 0.065, 0.07, 0.075, 0.08, 0.085, 0.09, 0.095, 0.1, 0.15, 0.2, 0.25, 0.3, or 0.35 uM or cystathionine may be increased to be between 0.05 and 0.35 uM. As another non-limiting example, the amount of cysteine may be increased to be above 140, 150, 160, 170, 180, 190, 200, 210, 220, 230, 240, 250, 260, 270, 280, 290, 300, 310, 320, 330, 340, 350, 360, 370, 380, 390, 400 or cysteine may be increased to be between 200 uM and 400 uM.

In one embodiment, the PEGylated htCBS or PEGylated htCBS mutant described herein may be used to cause a change such as a decrease in metabolite levels. As a non-limiting example, the metabolite may be homocysteine, methionine and S-adenosyl homocysteine which may be decreased by 5%, 10%, 15%, 20%, 25%, 30%, 33%, 35%, 40%, 45%, 50%, 52% 55%, 60%, 65%, 67%, 69%, 70%, 74%, 75%, 76%, 77%, 80%, 85%, 90%, 95%, 99% or 100%. As a non-limiting example, the amount of homocysteine may be decreased to be about 100, 95, 90, 85, 80, 75, 70, 65, 60, 55, 50, 45, 40, 35, 30, 25, 20, 15, 10, 5, 4, 3, 2 or 1 uM. As a non-limiting example, the amount of methionine may be decreased to be about 50, 45, 40, 35, 30, 25, 20, 15, 10, 5, 4, 3, 2 or 1 uM. As another non-limiting example, the amount of S-adenosyl homocysteine is decreased to be about 0.15, 0.14, 0.13, 0.12, 0.11, 0.10, 0.095, 0.09, 0.085, 0.08, 0.075, 0.07, 0.065, 0.06, 0.055, 0.05, 0.045, 0.04, 0.035, 0.03, 0.025, 0.02, 0.015, 0.01, 0.009, 0.008, 0.007, 0.006, 0.005, 0.004, 0.003, 0.002, 0.001 or less than 0.001 uM.

In one embodiment, the PEGylated htCBS or PEGylated htCBS mutant described herein may be used to reduce levels of homocysteine, methionine, S-adenosyl-methionine and S-adenosyl-homocysteine in a subject.

In one embodiment, the PEGylated htCBS or PEGylated htCBS mutant may be used to increase the levels of cysteine and cystathionine in a subject.

In a further aspect the present invention relates to a method to recombinantly produce and purify a human cystathionine synthase. The method includes the step of cloning a nucleic acid sequence encoding a human CBS enzyme or a truncated or mutated variant thereof into an expression vector. As a non-limiting example, the enzyme and method may be as set forth in International publication WO2014120770, the contents of which are herein incorporated by reference, and specifically as in SEQ ID NO: 01, SEQ ID NO: 02, SEQ ID NO: 3, SEQ ID NO: 4, SEQ ID NO: 13, SEQ ID NO: 14, SEQ ID NO: 15, and SEQ ID NO: 16.

Administration and Dosing

In one embodiment, PEGylated htCBS or PEGylated htCBS mutant may be administered to a subject by parenteral administration.

In one embodiment, PEGylated htCBS or PEGylated htCBS mutant may be administered to a subject by subcutaneous (SQ), intravenous (IV) or intraperitoneal (IP) injection. As a non-limiting example, PEGylated htCBS or PEGylated htCBS mutant may be administered to a subject by subcutaneous administration. As a non-limiting example, PEGylated htCBS or PEGylated htCBS mutant may be administered to a subject by intravenous administration. As a non-limiting example, PEGylated htCBS or PEGylated htCBS mutant may be administered to a subject by intraperitoneal administration.

In one embodiment, the PEGylated htCBS or PEGylated htCBS mutant may be administered to a subject at least 1, 2, 3, 4, 5, 6, 7, 8, 9, 10, 11, 12, 13, 14, 15, 16, 17, 18, 19, 20 or more than 20 times.

In one embodiment, the administration of the PEGylated htCBS or PEGylated htCBS mutant may be repeated every minute, 2 minutes, 3 minutes, 4 minutes, 5 minutes, six 6, 7 minutes, 8 minutes, 9 minutes, 10 minutes, 15 minutes, 20 minutes, 25 minutes, 30 minutes, 35 minutes, 40 minutes, 45 minutes, 50 minutes, 55 minutes, hourly, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, daily, 2 days, 3 days, 4 days, 5 days, 6 days, weekly, biweekly, 3 weeks, monthly, 2 months, quarterly, 4 months, 5 months, 6 months, 7 months, 8 months, 9 months, 10 months, 11 months, yearly, 13 months, 14 months, 15 months, 16 months, 17 months, or 18 months.

In one embodiment, the administration of the PEGylated htCBS or PEGylated htCBS mutant may be a series of doses which are minutes, hours, days or weeks apart. The number of doses in a series may be 2, 3, 4, 5 or 6. As a non-limiting example, a subject is administered 3 doses 24 hours apart. As another non-limiting example, a subject is administered 5 doses 12 hours apart.

In one embodiment, the administration of the PEGylated htCBS or PEGylated htCBS mutant may follow a dosing schedule of a series of doses that has a gap between the first series and the second series of doses. The gap between the doses may be 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, day, 2 days, 3 days, 4 days, 5 days, 6 days, week, 2 weeks, 3 weeks, monthly, 2 months, quarterly, 4 months, 5 months, 6 months, 7 months, 8 months, 9 months, 10 months, 11 months, 12 months, 13 months, 14 months, 15 months, 16 months, 17 months, or 18 months. The number of doses in a series may be 2, 3, 4, 5 or 6. As a non-limiting example, a subject may be administered a first series of 5 doses 12 hours apart and then 14 days after the first dose a subject is administered a second series of 5 doses 12 hours apart. As another non-limiting example, a subject is administered two series of doses over a period of 8 weeks where the first series is one dose twice a week for two weeks and the second series of doses is three times a week for 6 weeks.

In one embodiment, PEGylated htCBS or PEGylated htCBS mutant may be administered at least once after a subject has been administered Betaine. The time between the Betaine administration the PEGylated htCBS may be 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, day, 2 days, 3 days, 4 days, 5 days, 6 days, week, 2 weeks, 3 weeks, monthly, 2 months, quarterly, 4 months, 5 months, 6 months, 7 months, 8 months, 9 months, 10 months, 11 months, 12 months, 13 months, 14 months, 15 months, 16 months, 17 months, or 18 months. As a non-limiting example, the PEGylated htCBS may be administered 14 days after the subject was administered Betaine. As another non-limiting example, a subject may be administered two doses after the subject was administered Betaine. The PEGylated htCBS or PEGylated htCBS mutant may be administered 14 and 15 days after Betaine administration.

In one embodiment, PEGylated htCBS or PEGylated htCBS mutant may be administered in combination with Betaine to a subject. The combination may be administered at least 1, 2, 3, 4, 5, 6, 7, 8, 9, 10, 11, 12, 13, 14, 15 or more than 15 times.

In one embodiment, PEGylated htCBS or PEGylated htCBS mutant may be administered in combination with Betaine to a subject after the subject has initially received Betaine. The time between the combination treatment and the original Betaine administration may be 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, day, 2 days, 3 days, 4 days, 5 days, 6 days, week, 2 weeks, 3 weeks, monthly, 2 months, quarterly, 4 months, 5 months, 6 months, 7 months, 8 months, 9 months, 10 months, 11 months, 12 months, 13 months, 14 months, 15 months, 16 months, 17 months, or 18 months. As a non-limiting example, the combination may be administered 14 days after the subject was first administered Betaine. As another non-limiting example, a subject may be administered two doses after the subject was first administered Betaine. The combination may be administered 14 and 15 days after Betaine administration.

In one embodiment, the dose of PEGylated htCBS or PEGylated htCBS mutant administered to a subject may be between 5 and 8 mg/kg such as 5 mg/kg, 5.5 mg/kg, 6 mg/kg, 6.5 mg/kg, 7 mg/kg, 7.5 mg/kg or 8 mg/kg.

In one embodiment, the PEGylated htCBS or PEGylated htCBS mutant may be co-administered with another therapeutic for treating CBSDH. As used herein, "co-administered" means the administration of two or more components. These components for co-administration include, but are not limited to PEGylated htCBS, PEGylated htCBS mutant, betaine or Vitamin B6. Co-administration refers to the administration of two or more components simultaneously or with a time lapse between administration such as 1 second, 5 seconds, 10 seconds, 15 seconds, 30 seconds, 45 seconds, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes, 30 minutes, 31 minutes, 32 minutes, 33 minutes, 34 minutes, 35 minutes, 36 minutes, 37 minutes, 38 minutes, 39 minutes, 40 minutes, 41 minutes, 42 minutes, 43 minutes, 44 minutes, 45 minutes, 46 minutes, 47 minutes, 48 minutes, 49 minutes, 50 minutes, 51 minutes, 52 minutes, 53 minutes, 54 minutes, 55 minutes, 56 minutes, 57 minutes, 58 minutes, 59 minutes, 1 hour, 1.5 hours, 2 hours, 2.5 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 1.5 days, 2 days, or more than 3 days.

Definitions

As used in this specification, the singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

Where a range of values is provided, it is intended that each intervening value between the upper and lower limit of that range and any other stated or intervening value in that stated range is encompassed within the disclosure and specifically disclosed. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

"Coding sequence" refers to that portion of a nucleic acid (e.g., a gene) that encodes (i) an mRNA that is translated into an amino acid sequence of a protein; or (ii) a functional RNA, such as an interfering RNA or antisense molecule.

"Recombinant," when used with reference to, e.g., a cell, nucleic acid, polypeptide, expression cassette or vector, refers to a material, or a material corresponding to the natural or native form of the material, that has been modified by the introduction of a new moiety or alteration of an existing moiety, or is identical thereto but produced or derived from synthetic materials. For example, recombinant cells express genes that are not found within the native (non-recombinant) form of the cell (i.e., "exogenous nucleic acids") or express native genes that are otherwise expressed at a different level, typically, under-expressed or not expressed at all.

Recombinant techniques can include, e.g., use of a recombinant nucleic acid such as a cDNA encoding a protein or an antisense sequence, for insertion into an expression system, such as an expression vector; the resultant construct is introduced into a cell, and the cell expresses the nucleic acid, and the protein, if appropriate. Recombinant techniques also encompass the ligation of nucleic acids to coding or promoter sequences from different sources into one expression cassette or vector for expression of a fusion protein, constitutive expression of a protein, or inducible expression of a protein.

The terms "subject", "individual" or "patient" are used interchangeably herein and refer to a vertebrate, preferably a mammal. Mammals include, but are not limited to, humans.

"Associated" refers to coincidence with the development or manifestation of a disease, condition or phenotype. Association may be due to, but is not limited to, genes responsible for housekeeping functions whose alteration can provide the foundation for a variety of diseases and conditions, those that are part of a pathway that is involved in a specific disease, condition or phenotype and those that indirectly contribute to the manifestation of a disease, condition or phenotype.

"Physiological conditions" or "physiological solution" refers to an aqueous environment having an ionic strength, pH, and temperature substantially similar to conditions in an intact mammalian cell or in a tissue space or organ of a living mammal. Typically, physiological conditions comprise an aqueous solution having about 150 mM NaCl, pH 6.5-7.6, and a temperature of approximately 22-37 degrees C. Generally, physiological conditions are suitable binding conditions for intermolecular association of biological macromolecules. For example, physiological conditions of 150 mM NaCl, pH 7.4, at 37 degrees C. are generally suitable.

"Pharmaceutically acceptable excipient or carrier" refers to an excipient that may optionally be included in the compositions of the invention and that causes no significant adverse toxicological effects to the patient. In particular, in the present instance, such refers to an excipient that can be taken into the mammalian subject's body in association with an active compound (here PEGylated htCBS) with no significant adverse toxicological effects to the subject.

The term "excipient" or "vehicle" as used herein means any substance, not itself a therapeutic agent, used as a carrier for delivery of a therapeutic agent and suitable for administration to a subject, e.g. a mammal or added to a pharmaceutical composition to improve its handling or storage properties or to permit or facilitate formation of a dose unit of the composition into a discrete article such as a capsule or tablet suitable for oral administration. Excipients and vehicles include any such materials known in the art, e.g., any liquid, gel, solvent, liquid diluent, solubilizer, or the like, which is nontoxic and which does not interact with other components of the composition in a deleterious manner. Administration can mean oral administration, inhalation, enteral administration, feeding or inoculation by intravenous injection. The excipients may include standard pharmaceutical excipients, and may also include any components that may be used to prepare foods and beverages for human and/or animal consumption, feed or bait formulations or other foodstuffs.

"Permeant," "drug," or "pharmacologically active agent" or any other similar term means any chemical or biological material or compound, inclusive of peptides, suitable for administration by the methods previously known in the art and/or by the methods taught in the present disclosure, that induces a desired biological or pharmacological effect, which may include, but is not limited to (1) having a prophylactic effect on the organism and preventing an undesired biological effect such as preventing an infection, (2) alleviating a condition caused by a disease, for example, alleviating pain or inflammation caused as a result of disease, and/or (3) either alleviating, reducing, or completely eliminating the disease from the organism. The effect may be local, such as providing for a local anaesthetic effect, or it may be systemic. This disclosure is not drawn to novel permeants or to new classes of active agents. Rather it is limited to the mode of delivery of agents or permeants which exist in the state of the art or which may later be established as active agents and which are suitable for delivery by the present disclosure.

The term "about," particularly in reference to a given quantity, is meant to encompass deviations of plus or minus five percent.

"Optional" or "optionally" means that the subsequently described circumstance may or may not be present or occur, so that the description includes instances where the circumstance is present or occurs and instances where it is not present or does not occur.

"Substantially absent" or "substantially free" of a certain feature or entity means nearly totally or completely absent the feature or entity. For example, for a subject administered PEGylated htCBS, the substantial absence of an observable side effect means that such side effect is either non-detectable, or occurs only to a negligible degree, e.g., to an extent or frequency that is reduced by about 50% or more when compared to either the frequency or intensity of the same side effect observed in an untreated patient.

The terms "pharmacologically effective amount" or "therapeutically effective amount" as related to the present composition refer to a non-toxic, but sufficient amount of the active agent (or composition containing the active agent) to provide the desired level in the bloodstream or at the site of action (e.g. intracellularly) in the subject to be treated, and/or to provide a desired physiological, biophysical, biochemical, pharmacological or therapeutic response, such as amelioration of the manifestations of homocystinuria. The exact amount required will vary from subject to subject, and will depend on numerous factors, such as the active agent, the activity of the composition, the delivery device employed, the physical characteristics of the composition, intended patient use (i.e., the number of doses administered per day), as well as patient considerations, such as species, age, and general condition of the subject, the severity of the condition being treated, additional drugs being taken by the subject, mode of administration, and the like. These factors and considerations can readily be determined by one skilled in the art, based upon the information provided herein. An appropriate "effective" amount in any individual case may be determined by one of ordinary skill in the art using routine experimentation, based upon the information provided herein.

The term "biological activity" refers to any biological activity typically attributed to a nucleic acid or protein by those skilled in the art. Examples of biological activities are enzymatic activity, ability to dimerize, fold or bind another protein or nucleic acid molecule, etc.

The term "nucleic acid" may be in the form of RNA or in the form of DNA, and include messenger RNA, synthetic RNA and DNA, cDNA, and genomic DNA. The DNA may be double-stranded or single-stranded, and if single-stranded may be the coding strand or the non-coding (anti-sense, complementary) strand.

As used herein, a "variant" is a nucleic acid, protein or polypeptide which is not identical to, but has significant homology (for example, 80%, 85%, 90%, 91%, 92%, 93%, 94%, 95%, 96%, 97%, 98% or 99% sequence identity) over the entire length of the wild type nucleic acid or amino acid sequence, as exemplified by sequences in the public sequence databases, such as GenBank. As used herein, a "protein, polypeptide or peptide fragment thereof" means the full-length protein or a portion of it having an amino acid sequence usually at least 5, 6, 7, 8, 9, 10, 11, 12, 13, 14 or 15 amino acids in length, although dipeptides, tripeptides and tetrapeptides are also contemplated and encompassed by the present disclosure.

As used herein, a "mutant" is a mutated protein designed or engineered to alter properties or functions relating to glycosylation, protein stabilization and/or ligand binding.

As used herein, the terms "native" or "wild-type" relative to a given cell, polypeptide, nucleic acid, trait or phenotype, refers to the form in which that is typically found in nature.

As used herein, the terms "protein," "polypeptide," "oligopeptide" and "peptide" have their conventional meaning and are used interchangeably to denote a polymer of at least two amino acids covalently linked by an amide bond, regardless of length or post-translational modification (e.g., glycosylation, phosphorylation, lipidation, myristilation, ubiquitination, etc.). Furthermore, the polypeptides described herein are not limited to a specific length. Included within this definition are D- and L-amino acids, and mixtures of D- and L-amino acids. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Polypeptides can also refer to amino acid subsequences comprising epitopes, i.e., antigenic determinants substantially responsible for the immunogenic properties of a polypeptide and being capable of evoking an immune response.

"Position corresponding to" refers to a position of interest (i.e., base number or residue number) in a nucleic acid molecule or protein relative to the position in another reference nucleic acid molecule or protein. Corresponding positions can be determined by comparing and aligning sequences to maximize the number of matching nucleotides or residues, for example, such that identity between the sequences is greater than 90%, greater than 95%, greater than 96%, greater than 97%, greater than 98% or greater than 99%. The position of interest is then given the number assigned in the reference nucleic acid molecule. For example, if a particular polymorphism in Gene-X occurs at nucleotide 2073 of SEQ ID No. X, to identify the corresponding nucleotide in another allele or isolate, the sequences are aligned and then the position that lines up with 2073 is identified. Since various alleles may be of different length, the position designate 2073 may not be nucleotide 2073, but instead is at a position that "corresponds" to the position in the reference sequence.

"Percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)). Examples of algorithms that are suitable for determining percent sequence identity and sequence similarity are the BLAST and BLAST 2.0 algorithms, which are described in Altschul et al. (1990) *J. Mol. Biol.* 215:403-410 and Altschul et al. (1977) *Nucleic Acids Res.* 3389-3402, respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as "seeds" for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

While all of the above mentioned algorithms and programs are suitable for a determination of sequence alignment and % sequence identity, for purposes of the disclosure herein, determination of % sequence identity will typically be performed using the BESTFIT or GAP programs in the GCG Wisconsin Software package (Accelrys, Madison WI), using default parameters provided.

The term "NH2 Terminal Modifications" may be used to refer to the peptides described herein. The terminus of the peptide compounds of the invention corresponding to the amino terminus, if present, may be in the "free" form (e.g., H2N−), or alternatively may be acylated with a group of the formula $R^2C(O)$— or $R^2S(O)_2$—, wherein $R^2$ is as previously defined. In one embodiment, $R^2$ is selected from the group consisting of $(C_1\text{-}C_6)$ alkyl, $(C_5\text{-}C_{10})$ aryl, $(C_6\text{-}C_{16})$ arylalkyl, 5-10 membered heteroaryl or 6-16 membered heteroarylalkyl.

In another embodiment, the amino terminus may be "blocked" with a blocking group designed to impart the compound with specified properties, such as a low antigenicity. Non-limiting examples of such blocking groups include polyalkylene oxide polymers such as polyethylene glycol (PEG). A variety of polymers useful for imparting compounds, and in particular peptides and proteins, with specified properties are known in the art, as are chemistries suitable for attaching such polymers to the compounds. Specific non-limiting examples may be found in U.S. Pat. Nos. 5,643,575; 5,730,990; 5,902,588; 5,919,455; 6,113,906; 6,153,655; and 6,177,087, the disclosures of which are incorporated herein by reference.

The term "Carboxy Terminus Modifications" may be used in relation to the peptides described herein. The terminus of the peptide compounds corresponding to the C-terminus, if present, may be in the form of an underivatized carboxyl group, either as the free acid or as a salt, such as a sodium, potassium, calcium, magnesium salt or other salt of an inorganic or organic ion, or may be in the form of a derivatized carboxyl, such as an ester, thioester or amide. Such derivatized forms of the compounds may be prepared by reacting a compound having a carboxyl terminus with an appropriate alcohol, thiol or amine. Suitable alcohols, thiols or amines include, by way of example and not limitation, alcohols of the formula $R^2OH$, thiols of the formula $R^2SH$ and amines of the formula $R^2NH_2$, $R^2R^2NH$ or $NH_3$, where each $R^2$ is, independently of the others, as previously defined.

The term "L or D form amino acids" may be used in relation to the peptide described herein. As will be recognized by skilled artisans, the various X″ residues comprising the compounds of the invention may be in either the L- or D-configuration about their $C_\alpha$ carbons. In one embodiment, all of the $C_\alpha$ carbons of a particular compound are in the same configuration. In some embodiments of the invention, the compounds comprise specific chiralities about one or more $C_\alpha$ carbon(s) and/or include non-peptide linkages at specified locations so as to impart the compound with specified properties. For example, it is well-known that peptides composed in whole or in part of D-amino acids are more resistant to proteases than their corresponding L-peptide counterparts. Thus, in one embodiment, the compounds are peptides composed in whole or in part of D-amino acids. Alternatively, compounds having good stability against proteases may include peptide analogs including peptide linkages of reversed polarity at specified positions. For example, compounds having stability against tryptic-like proteases include peptide analogs having peptide linkages of reversed polarity before each L-Arg or L-Lys residue; compounds having stability against chymotrypsin-like proteases include peptide analogs having peptide linkages of reversed polarity before each small and medium-sized L-aliphatic residue or L-non-polar residue. In another embodiment, compounds having stability against proteases include peptide analogs composed wholly of peptide bonds of reversed polarity. Other embodiments having stability against proteases will be apparent to those of skill in the art. Additional specific embodiments of the compounds are described herein.

EXAMPLES

The following examples are illustrative in nature and are in no way intended to be limiting.

Example 1. Experimental Procedures

A. Construction of Sequence-Optimized, Truncated Human CBS in PET29A(+) Vector As previously described in International Publication No. WO2014120770, the disclosure of which is incorporated herein by reference in its entirety, full length (551 aa) human CBS coding sequence was optimized for bacterial expression and cloned into the pUC57 vector following digestion with the EcoRV restriction enzyme, by GenScript USA Inc (NJ, USA). The CBS sequence was then amplified by PCR using primers A1 and A2 to generate a sequence coding for the truncated enzyme (aa 1-413). The PCR product was then digested with the restriction enzymes NcoI and XhoI, and ligated into the pET-28a(+) vector that was digested with the same enzymes. Cloning into the optimal NcoI site of pET-28a(+) results in a G to C mutation as compared to the CBS wild-type sequence. Site-Directed Mutagenesis kit (Stratagene, CA, USA) utilizing primers B1 and B2, was used to re-generate the wild type sequence (htCBS). The same strategy was used to generate the C15S mutant (T to A mutation; htCBSC15) by using primers C1 and C2. All sequences were verified by sequencing. Expression of the truncated CBS is controlled by an upstream T7 promoter in the pET-28a(+) vector, which requires transformation into DE3 bacteria and induction by IPTG. Table 1 describes the primers and their sequence identifier.

TABLE 1

| Primers | |
|---|---|
| Primer name | SEQ ID NO. |
| A1 | 7 |
| A2 | 8 |
| B1 | 9 |
| B2 | 10 |
| C1 | 11 |
| C2 | 12 |
| pKK-F (SphI) | 5 |
| pKK-R (Kpn I) | 6 |

B. Expression and Purification

The pET-28a(+) vector, harboring the sequence coding for the truncated human CBS, was transformed into DE3 bacteria, i.e., *E. coli* BL-21 (DE3) or HMS174(DE3), and bacteria from kanamycin-resistant clones were grown in 5 ml of Luria-Bertani (LB) medium, with 30 ug/ml kanamycin, overnight at 37° C. on a rotational shaker at 275 RPM. One ml of the overnight culture was added to a 100 ml Terrific Broth (TB) medium with 30 ug/ml kanamycin and grown overnight. 10 ml of was then added to a 1 liter TB medium containing 0.001% of thiamine-HCl pH 8.0, 0.0025% of pyridoxine-HCl pH 8.0, 0.3 mM δ-ALA pH 8.0, 150 μM ferric chloride, 30 ug/ml of kanamycin. The culture was then grown at 30° C. on a rotational shaker at 275 RPM until OD600 reached the value of ~0.6-0.7 and protein expression was induced by addition of 1 mM IPTG. Fermentation was continued for additional 16 hours. Cells were harvested by a 10 minutes, 6000 RCF centrifugation at 4° C., washed with ice-cold 0.9% NaCl, re-centrifuged as above, and frozen at −80° C. 4.45 ml of lysis buffer (20 mM $NaH_2PO_4$, PH=7.2, 40 mM NaCl, 0.1 mM PLP) per 1 gram of pellet was then added to the cell pellet and the latter was homogenized in a Dounce homogenizer and treated with lysozyme (2 mg/ml final), incubated for 1 hour at 4° C. on a rocking platform, sonicated to reduce viscosity, and centrifuged at 53000 RCF. The supernatant, comprising the soluble fraction was then stored at −80° C. The lysate was processed through a multi-step chromatographic procedure. The core process consists of an anion exchange capture column (DEAE Sepharose-FF), followed by an affinity column. This attains purity of approximately 90%. The final purity of >99% is achieved by the use of one or two polishing chromatography steps. The final column eluate was diafiltered into PBS.

C. Enzyme Activity Assay

CBS activity was determined by a radioisotope assay with $C^{14}$-labeled serine as a substrate. Ten μl (total 490 ng) of pure htCBS in dilution buffer (0.1 M Tris-HCl pH=8.6, 1 mM DTT, 10 μM PLP, 0.5 mg/ml BSA) or 10 μl of plasma were added to 85 μl of reaction mixture containing 0.1 M Tris-HCl pH=8.6, 10 mM L-serine, 0.5 mM PLP, 0.5 mg/ml BSA and 0.3 μCi (for pure enzyme) or 0.45 μCi (for plasma) of L-[$C^{14}$(U)]-Serine. Samples were incubated for 5 min at 37° C. and reaction was initiated by addition of 5 μl of 0.2 M Hcy (10 mM final concentration). Following 30 min of incubation at 37° C., a 20 μl aliquot of the assay mixture was applied onto a grade 3 CHR Whatman (NJ, USA) paper. The $C^{14}$-cystathionine formed in the reaction was separated from $C^{14}$-serine by an overnight descending paper chromatography in 2-propanol/formic acid/$H_2O$ (75:5.7:18.9 v/v). Radioactivity in the area of the marker cystathionine (detected by staining the marker lane with ninhydrin) was determined by cutting the chromatogram into strips that were submerged in 5 ml of Opti-fluor scintillation cocktail (PerkinElmer, MA, USA) and counted in a Beckman LS-3801 scintillation counter. For pure enzyme, specific activity values are expressed as enzyme units (the amount of enzyme that produces 1 μmol of cystathionine/hour) per mg of CBS, and for plasma samples as units per μl plasma.

D. In Gel Activity Assay

Protein samples were separated using Native Page (Bio-Rad, CA, USA). The gel was then incubated for 15-30 minutes in a staining solution (100 mM Tris-HCl pH=8, 20 mM L-cysteine, 50 mM 2-mercaptoethanol, 0.1 mM PLP and 0.2 lead nitrate). Reaction was stopped by submerging the gel in 7% acetic acid.

E. Determination of Metabolite Concentrations

Plasma metabolites homocysteine, cystathionine and cysteine were determined by stable-isotope-dilution liquid chromatography mass spectrometry as previously described in (Allen et al., 1993, *Metabolism,* 42:1448-1460). Measurements of total non-protein bound homocysteine and other aminothiols as well as of amino acids in tissue were performed as described in (Maclean et al., 2010b. *Mol. Genet. Metab.* 101, 153-162).

F. PEGylation

Polyethylene glycol molecules were purchased from the NOF Corporation (Tokyo, Japan). PEGylation was carried out according to manufacturer instructions. For example, coupling of PEG maleimide derivatives to the SH groups of htCBS (5 mg/ml) was carried out in a 100 mM phosphate buffer pH=6.5 overnight at 4° C. Molar Ratio between PEG molecules to the CBS protein was 10:1 or 5:1.

G. Animal Procedures

All animal procedures were approved by the University of Colorado-Denver IACUC, which is an AAALAC Accredited (#00235), Public Health Service Assured (#A 3269-01) and USDA Licensed (#84-R-0059) Institution. C576BL/6J and CBS knock out (KO) mice were obtained from the Jackson Laboratory (ME, USA). Human Only (HO) mice were previously generated (Maclean et al., 2010b. *Mol. Genet. Metab.* 101, 153-162). Animals were maintained on extruded standard diet 2920X (Harlan, CA, USA). Representative pups were routinely analyzed for homozygosity. A single-use lancet for submandibular bleeding was used for blood collection into Capiject T-MLHG lithium heparin (12.5 IU) tubes with gel (Terumo Medical Corporation, NJ, USA). Tubes were then centrifuged at 1200 G for 10 min, followed by collection of plasma to 1.5 ml tubes and storage at −80° C.

Genotyping: Representative pups were routinely analyzed for homozygosity qPCR. Tail biopsies were generated by the DNeasy Blood and Tissue kit (Qiagen, Hilden, Germany). DNA quality was monitored by NanoDrop 1000 (Thermo Scientific, DE, USA). Twenty ng samples of DNA were run single-plex in triplicate using Applied Biosystem's (CA, USA) Gene Expression master mix (Item 190 4369016). Amplification was performed on Applied Biosystem's 7500 Fast Instrument using the standard curve method. Applied Biosystems' Tert (Item #4458366) or Tfrc (Item #4458368) copy number reference assays were used as the homozygous one copy calibrator. Applied Biosystem's assay Mr00299300 was used to detect the Neo gene.

Example 2. htCBS Retention Time

A. Unmodified htCBS Exhibits a Short Retention Time in Circulation

The pharmacokinetic properties of a pharmacologically active substance that is administered to circulation is greatly affected by natural mechanisms of ADME. Rapid clearance of the injected molecule may greatly impact treatment efficacy and thus longer circulating half-lives are desired, which may translate into less frequent administrations or smaller doses that in turn minimize the side effects. To determine the pharmacokinetics of htCBS in plasma circulation, a single dose of 5 mg/kg was injected via subcutaneous (SQ), intravenous (IV) or intraperitoneal (IP) routes to C57BL/6J mice. Administration of htCBS via IV or IP routes exhibited the highest specific activity values during the first 4 hours post injection (observed peak plasma levels of up to 123 and 76 mU/μL, respectively; Table 2 shows Area Under Curve (AUC) values). The pharmacokinetic parameters calculated from plasma samples (Table 2) show that the half-life for htCBS was 2.7 hours, suggesting that after roughly 6 half-lives (less than 20 hours) htCBS levels should be undetectable.

The bioavailablity of htCBS was 50% for SQ routes suggesting that SQ delivery may be a clinical option for this therapeutic approach. The slower apparent half-lives for SQ and IP (Table 2) can be explained by a slow absorption phase that is occurring during the elimination phase thereby extending the mean residency time and apparent half-life, however, for the present purpose a much longer half-life was desirable and thus PEGylated derivatives of htCBS were tested.

TABLE 2

| Pharmacokinetic Parameters | | | | |
| --- | --- | --- | --- | --- |
| Pharmacokinetic Parameter | Units | IP | SQ | IV |
| Dose Amount | Mg/Kg | 5 | 5 | 5 |
| AUC(0-t) (obs area) | mU-hr/μL | 932.4 | 500.9 | 1011 |
| Bioavailability | % | 92% | 50% | — |
| E Half-life | hr | 4.3 | 6.1 | 2.7 |
| Cmax (obs) | Mu/μL | 75.9 | 34.5 | — |
| MRT (area) | hr | 7.9 | 9.5 | 4.9 |

Figure 1B:
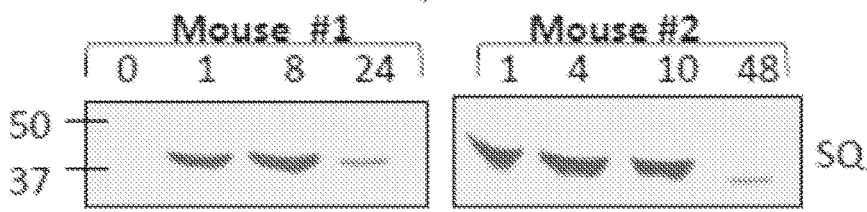
Figure 1B:
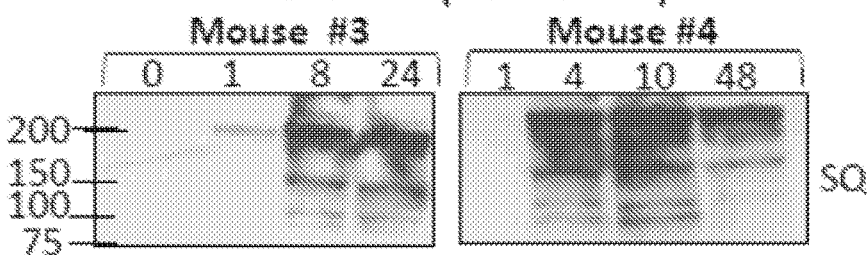

The rapid decline in htCBS activity in vivo may be attributed to a facilitated clearance from circulation and may also be attributed to the loss of enzymatic activity of htCBS once introduced to the environment in circulation. To test the latter, htCBS was incubated in vitro in mouse plasma of wild type or HO mice at 37° C. for up to 96 hours, with activity measured every 24 hours. As shown in FIG. 1A, no significant loss of activity was recorded for up to 72 hours of incubation in the plasma of either mouse model. A modest 25% loss of activity was recorded after 96 hours of incubation. Furthermore, as shown in FIG. 1B, western blot (WB) analyses of plasma from the SQ injected animals, revealed that the amount of htCBS decreases as a function of time, hence, clearance accounts for the rapid loss of htCBS activity in circulation, rather than loss of activity in plasma.

B. PEGylation of htCBS Enhances Plasma Half-Life in Vivo

In order to determine the impact of PEG molecules on the pharmacokinetics CBS, htCBS was PEGylated with a low molecular weight (2 kDa) linear PEG, and with a high molecular weight (40 kDa) four arm branched PEG (designated ME020MA and GL4-400MA, respectively). As shown in Table 3, PEGylation did not affect the specific activity of the enzyme. Table 3 shows the results of the Coomassie-stained SDS-PAGE of the PEGylated and non-PEGylated htCBS with corresponding specific activity values showing that PEGylation does not influence the activity of the enzyme. Mice were injected SQ as described in A (n=4-5), with the ME200MA- or GLA-400MA-PEGylated htCBS as compared to the non-PEGylated htCBS.

TABLE 3

| Activity | |
|---|---|
| htCBS tested | Specific Activity |
| Non-PEG CBS | 1193 |
| ME-200MA CBS | 1184 |
| GL4-400MA CBS | 1075 |

A dose of 5 mg/kg body weight (BW) of PEGylated htCBS (PEGhtCBS) was administered to C57BL/6J mice via the SQ and IV route, and CBS activity was monitored at different time points. Two experimental arms (n=5 each) were used for each injection route. Blood was collected post injection from group 1 at 0, 1, 8 and 24 hours and from group 2 at 1, 4, 10, and 48 hours.

As shown in FIG. 1B (bottom panel) for the GL4-400MA PEGhtCBS, the activity in plasma was significantly extended for the PEGylated protein as compared to the non-PEGylated counterpart. As shown in Table 4 the half-life increased from 2.7 hours for the non-PEGylated htCBS to 16.7 and 30.4 hours with the ME020MA and GLA-400MA PEGylation, respectively.

TABLE 4

| Pharmacokinetic Modeling Results | | | | |
|---|---|---|---|---|
| Pharmacokinetic Modeling Results | | PEGylated htCBS ME020MA | | PEGylated htCBS GL400MA |
| Parameter | Units | SQ | IV | SQ | IV |
| Dose Amount | Mg/Kg | 5 | 5 | 5 | 5 |
| AUC(0-t) (obs area) | Mu-hr/μL | 1637.0 | 3193.2 | 2286.3 | 2836.5 |
| Bioavailability | % | 51.2% | — | 80.6% | |
| E Half-life | hr | 15.1 | 16.7 | 20.1 | 30.4 |
| Cmax (obs) | Mu/μL | 54.6 | — | 64.9 | — |
| MRT (area) | hr | 27.0 | 25.7 | 37.0 | 43.1 |

This means that the time of exposure after a single dose would be 5 to 10-fold longer for the PEGylated forms. Additionally, the bioavailability after SQ administration ranged from 50 to 80% suggesting that the SQ route would be reasonable for clinical studies.

Example 3. Administration of htCBS and Serum Levels of Homocysteine, Cystathionine and Cysteine The ultimate goal for the use of htCBS for CBSDH is to lower the toxic tHcy load, to elevate cystathionine and cysteine levels. These changes are expected to prevent, reverse or delay the onset of CBSDH symptoms. Homocystinuria research, however, has long been hindered by a lack of a suitable animal model. Mice that are complete knockout for the mouse gene die within 2-3 weeks after birth. The HO (Human Only) mice are different from other knockout mice because, in addition to having the mouse gene knocked out, they express low levels of the human gene which allows their survival to adulthood (Maclean et al., 2010b. *Mol. Genet. Metab.* 101, 153-162). HO mice exhibit severe elevations of Hcy, methionine, S-adenosyl-methionine, and S-adenosylhomocysteine and present with a concomitant decrease in plasma and hepatic levels of cysteine. Accordingly these mice exhibit characteristics that in several aspects, recapitulate the disease as it occurs in humans.

A. htCBS Administration Does Not Improve tHcy and Cystathionine Concentrations

Figure 2:
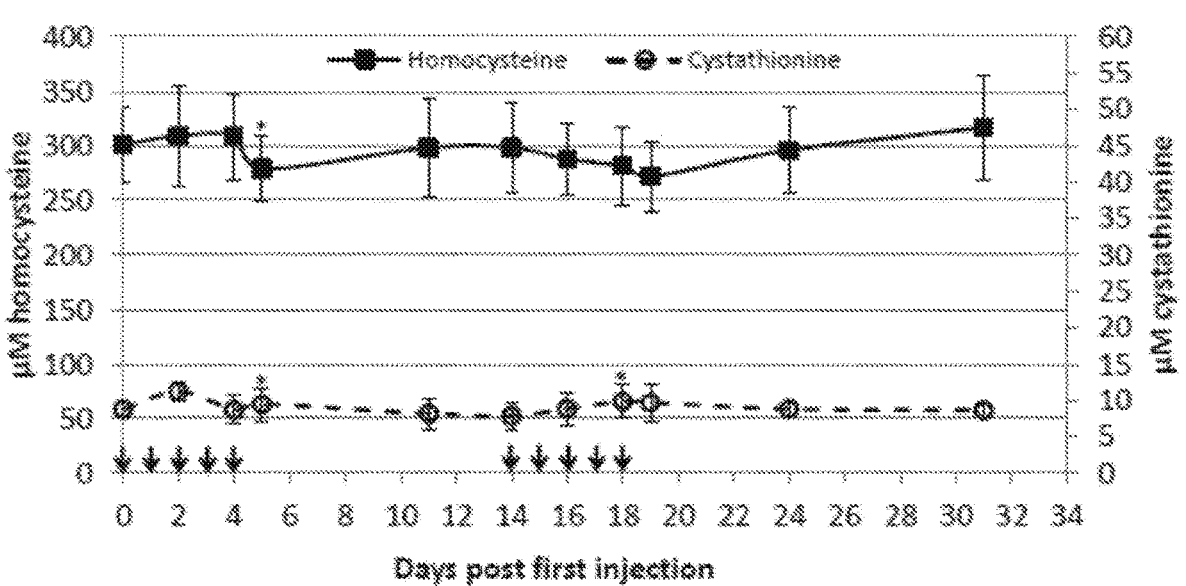
FIG. 2 shows that repeated administration of non-PEGylated htCBS results in no changes in homocysteine or cystathionine levels in HO mice.

HO mice administered non-PEGylated htCBS at 5 mg/kg for 5 consecutive days on weeks 1 and 3 (10 days between sets of treatments) demonstrated no change in serum homocysteine levels. FIG. 2 shows the mean homocysteine and cystathionine levels in HO mice. This lack of metabolic modulation by non-PEGylated htCBS further confirms the necessity to modify htCBS by covalent attachment of poly-ethylene glycol molecules.

Figure 3:
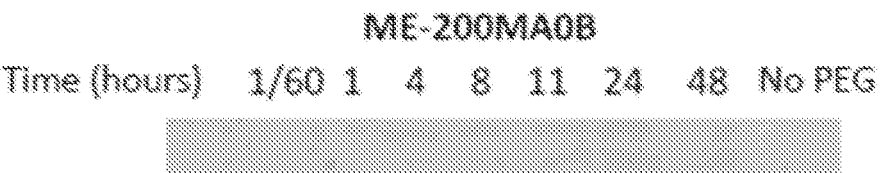
FIG. 3 shows a PEGylation time course with the selected linear 20 kDa PEG molecule designated ME200MAB.
Figure 3:
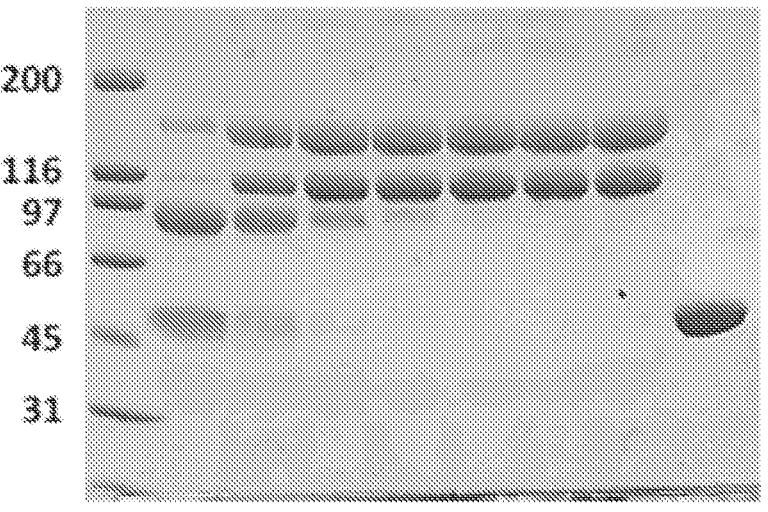

Several different chemistries of PEGs were tested as described in International Publication No. WO2014120770, the contents of which are herein incorporated by reference in its entirety, (See Table 5) and the data indicate that CBS that is PEGylated with lower than 20 kDa PEGs demonstrates a more rapid loss of activity in plasma, than CBS with PEGs of higher molecular weight. For that reason, the linear 20 kDa PEG designated ME200MAOB was chosen for further analyses. FIG. 3 presents a Coomassie-stained SDS-PAGE showing the time course of htCBS PEGylation with ME200MAOB. PEGylation reaction was initiated by adding the PEG, and samples were withdrawn from the tube at the indicated time points to be analyzed.

TABLE 5

| PEG chemistry evaluation | | | |
|---|---|---|---|
| PEG molecule | Structure | Target group | Size (kDa) |
| ME020MA | linear | —SH | 2 |
| ME050GS | linear | —NH2, —OH, —SH | 5 |
| ME200GS | linear | —NH2, —OH, —SH | 20 |
| ME200MA0B | linear | —SH | 20 |
| ME400MA | linear | —SH | 40 |
| GL2400MA | 2 arms | —SH | 40 |
| GL4400MA | 4 arms | —SH | 40 |
| GL2800MA | 4 arms | —SH | 80 |

B. Repeated PEGhtCBS Administration Improves tHcy and Cystathionine Concentrations and Restores Normal Cysteine Levels.

Figure 4A:
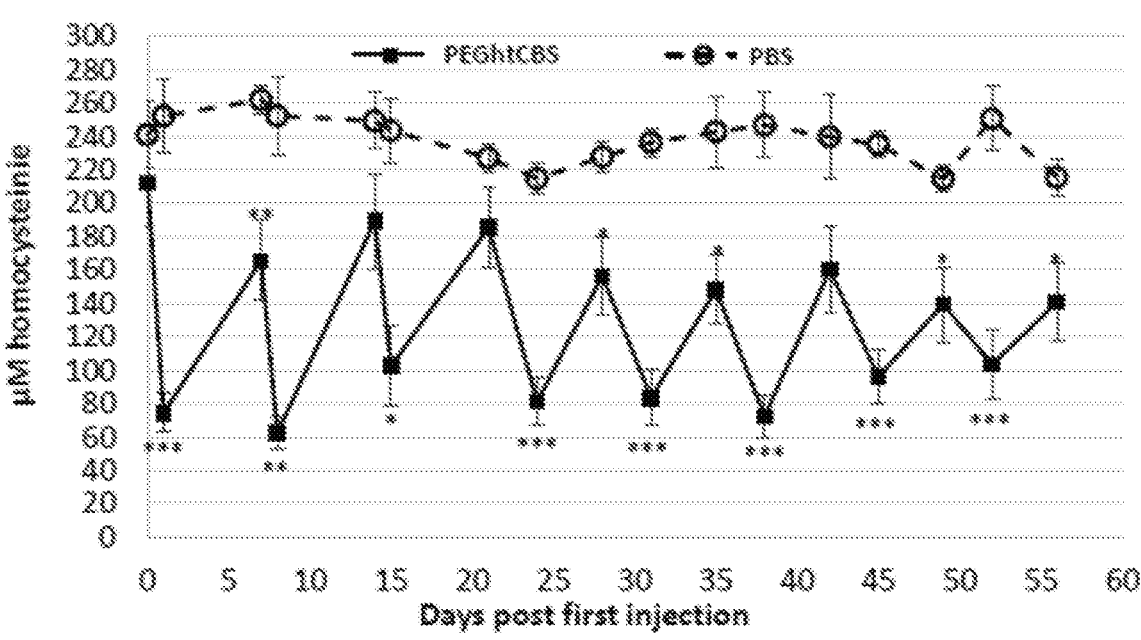
FIG. 4A-4D show that long term repeated injection of the PEGylated htCBS significantly impacts homocysteine, cystathionine and cysteine plasma and tissue levels.
Figure 4B:
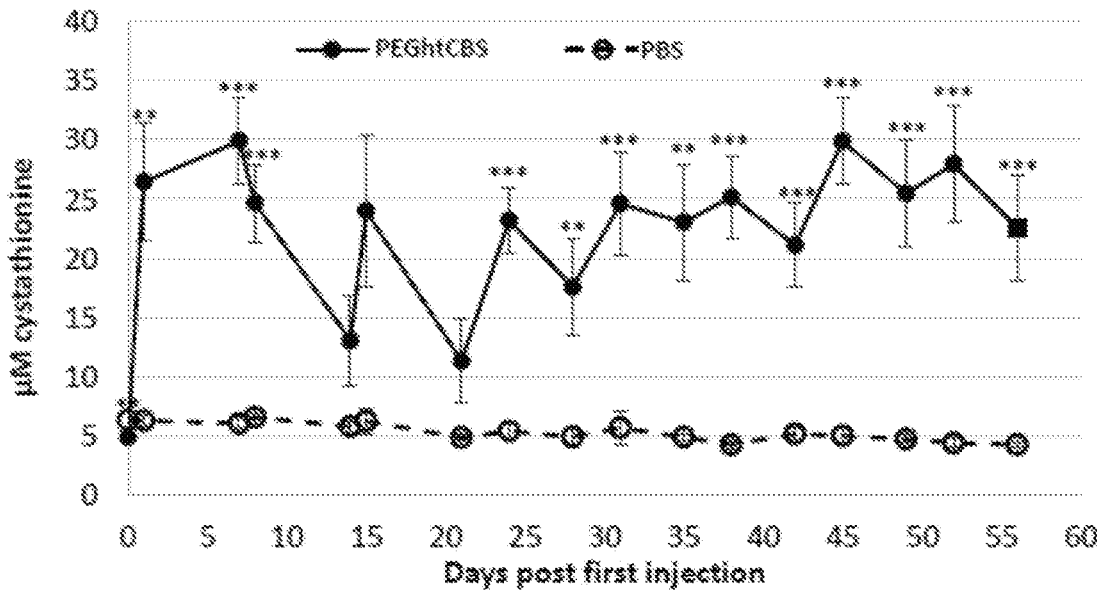
Figure 4C:
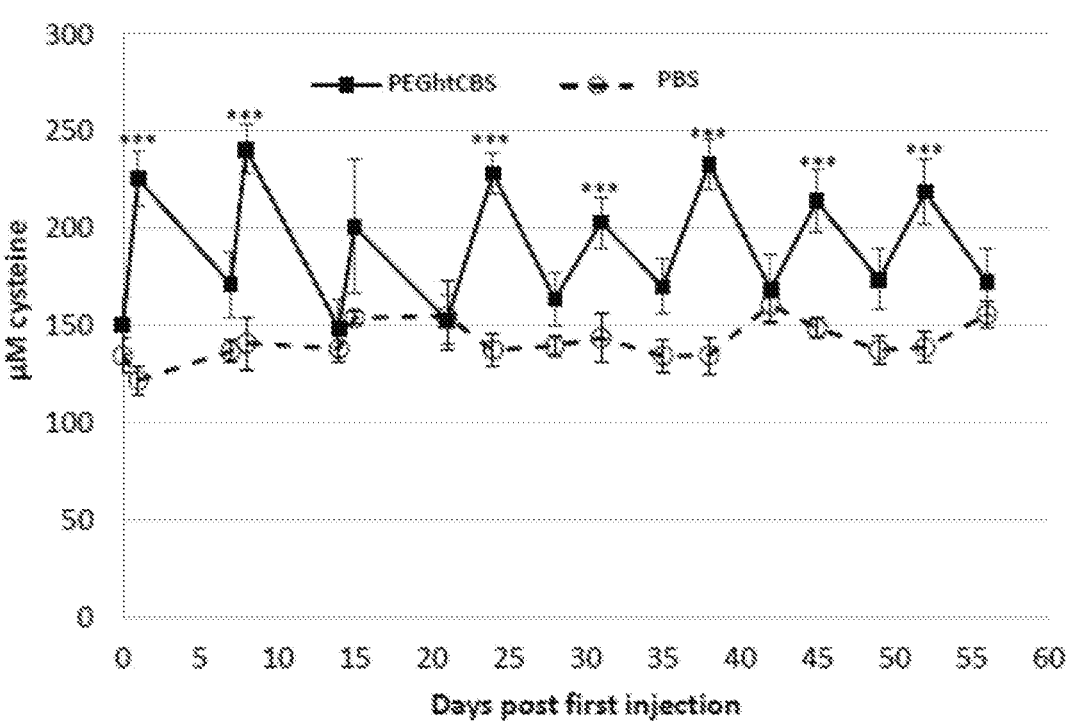
Figure 4D:
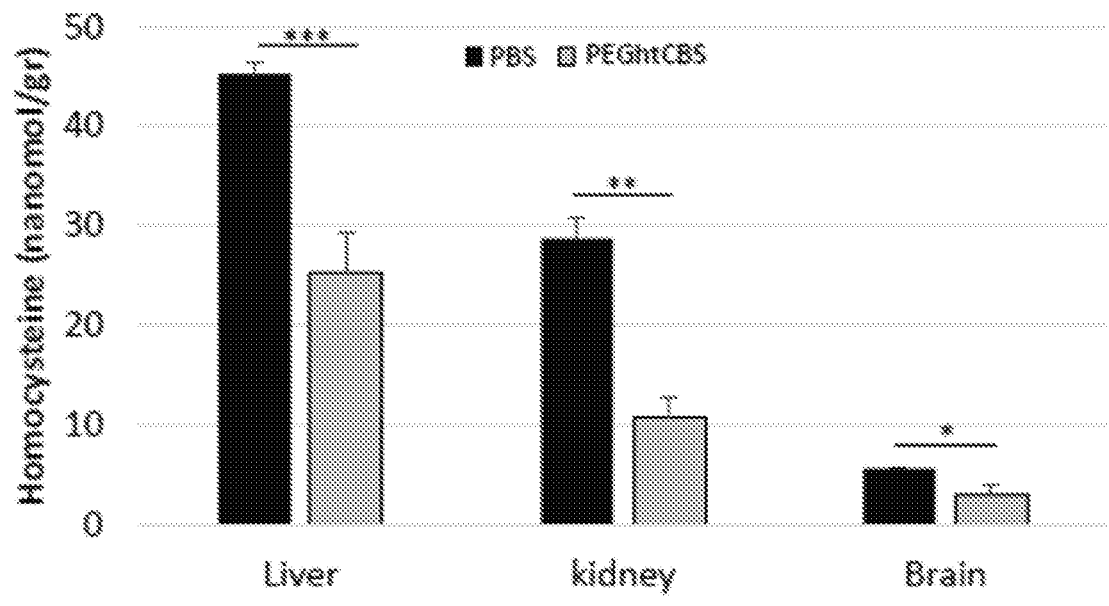

The long term effect of PEGhtCBS administration was monitored using HO mice. The PEGhtCBS enzyme was administered to 8 HO mice at a dose of 7.5 mg/kg, twice a week (Monday and Thursday) for the first two weeks, and then three times a week (Monday, Wednesday and Friday) for 6 weeks. Blood samples were collected 24 hours (Tuesday) and 72 hours (Monday) post injection (FIG. 4A-4C). FIG. 4A shows that plasma tHcy was reduced from 212 μM at time 0 to an average in the range of 62-103 μM 24 hours after injections, and was at a range of 141-189 μM 72 hours post the last weekly injection. From day 28 on, the 72 hour post injections values were significantly lower than the time 0 value (P≤0.02). Cystathionine and cysteine levels were positively influenced as well. Cystathionine increased from 6 μM to as high as 30 μM and cysteine was constantly above 200 μM 24 hours post injection (FIG. 4C). Interestingly, from day 24 on, fluctuations in cystathionine concentration were much less pronounced as compared to the first three weeks of treatment. In addition to analysis of plasma metabolites levels, liver, kidney and brain tissue samples from the injected mice were analyzed as well to determine the levels of non-protein bound homocysteine (free and disulfide-linked forms). As shown in FIG. 4D, in the long term injected animals, a reduction of 44%, 63% and 47% was demonstrated for liver, kidney, and brain tissues, respectively. Thus, long term repeated injection of the PEGhtCBS significantly impacts homocysteine, cystathionine and cysteine plasma levels.

Figure 5A:
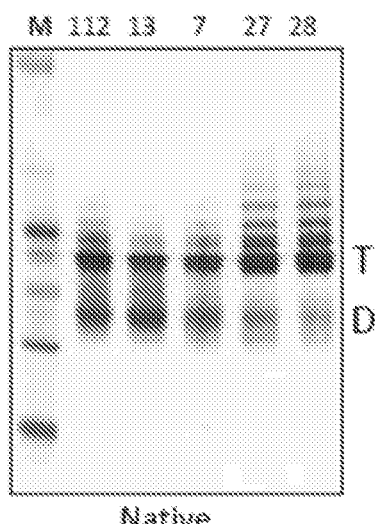
FIG. 5A-5H illustrate that the PEGylated htCBS mutant (also referred to as PEGC15S) and PEGylated htCBS prevents protein aggregation, forms mainly dimers and exhibits a reproducible PEGylation pattern.
Figure 5B:
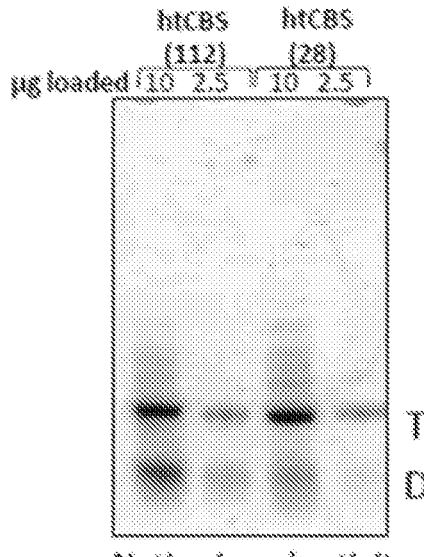
Figure 5C:
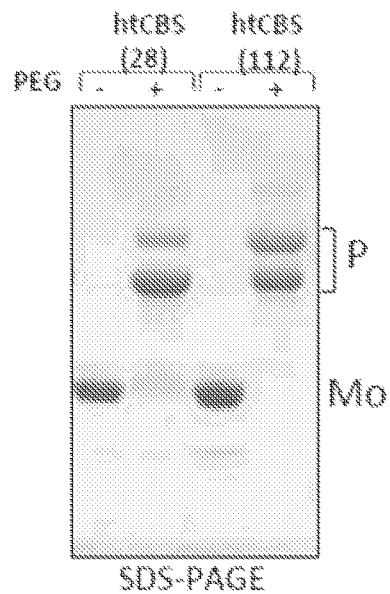
Figure 5D:
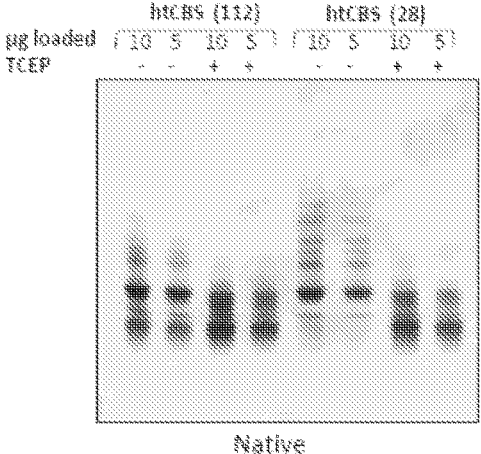
Figures 5E, 5F:
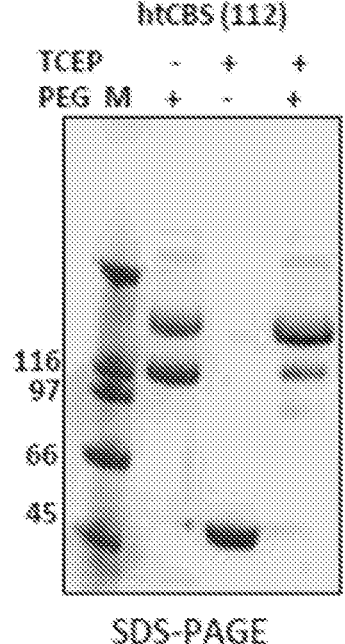
Figure 5G:
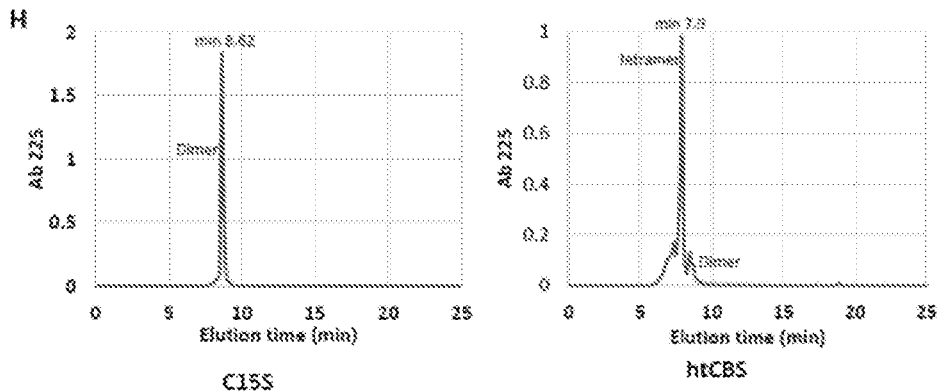
Figure 5H:
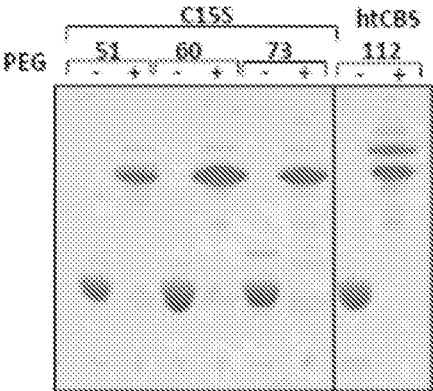

Example 4. htCBS Mutant (C15S) Shows Preferential Aggregation and Pegylation Patterns A. C15S Mutated htCBS Exhibits No Aggregation and a Uniform PEGylation Pattern Although it was previously reported that the htCBS enzyme is less prone to aggregation as compared to the full length protein (Frank et al., 2006, *Biochemistry* 45:11021-11029), it still forms tetramers and higher aggregates. This may stimulate immune defensive mechanisms and lead to e.g. amyloid deposition (D'Souza et al., 2014, "Amyloid: the international journal of experimental and clinical investigation. The official journal of the International Society of Amyloidosis" 21:71-75), but also affect purification, handling, and consistency. FIG. 5A (previously disclosed as FIG. 5A of WO2014120770, the contents of which are herein incorporated by reference in its entirety) depicts a Coomassie-stained native-PAGE showing that different batches of htCBS exhibited different dimer/tetramer ratios, with varying degrees of higher aggregates. FIG. 5B (previously disclosed as FIG. 5B of WO2014120770, the contents of which are herein incorporated by reference in its entirety) is an in-gel activity assay demonstrated that these aggregates exhibit CBS activity. FIG. 5C (previously disclosed as FIG. 5C of WO2014120770, the contents of which are herein are incorporated by reference in its entirety) shows that aggregation causes non-consistent PEGylation products. PEGylation resulted in two distinct bands, presumably reflecting varying degrees of PEGylation as aggregation may act to obscure the available PEGylation sites. Accordingly, due to a more pronounced aggregation of batch 28 (FIG. 5A) its PEGylation resulted in a more pronounced lower band, i.e less PEGylated, on SDS-PAGE (FIG. 5C), whereas PEGylation of batch 112, comprised of both tetramers and dimers (FIG. 5A), resulted in a more pronounced upper band as compared to batch 28 (FIG. 5C). FIG. 5D shows a Coomassic-stained native gel, indicating that incubation of both enzyme batches with the reducing agent tris(2-carboxyethyl) phosphine (TCEP) converted much of the tetramers and higher aggregates to a dimeric form. These data imply that aggregation is driven by exposed cysteines on the surface of htCBS. Thus, TCEP treatment was believed to also result in a more extensive PEGylation, as more dimers are generated from higher MW forms, giving rise to exposure of additional PEGylation sites on the surface of htCBS. Indeed, as shown in FIG. 5E the ratio between the upper/lower PEGylation bands on a Coomassic-stained SDS-PAGE is significantly shifted towards the upper band following TCEP treatment as compared to PEGylation in the absence of TCEP. Accordingly, htCBS aggregation is believed to be driven, at least partially, by formation of intramolecular disulfide bridges. Thus, C15 was mutated to serine, generating the C15S htCBS mutant; C15 was previously shown to be the most reactive cysteine on the surface of CBS (Frank et al., 2006, Biochemistry 45:11021-11029). FIG. 5F (previously disclosed as FIG. 6A of WO2014120770, the contents of which are herein incorporated by reference by its entirety) depicts a Coomassie-stained native gel, in which two main bands (dimers and tetramers) arc observed for htCBS whereas the C15S htCBS mutant exhibits a single band, which as expected is not affected by treatment with TCEP. This observation was further substantiated by HPLC size exclusion chromatography (HPLC-SEC). CBS preparations were separated on a Yarra SEC-3000, 300*7.8 mm size exclusion column (Phenomenex, CA, USA). The column was calibrated and operated in 100 mM sodium phosphate pH=6.8, at a flow rate of 1 ml/min at room temperature. HPLC-SEC analysis, FIG. 5G (previously disclosed as part of FIG. 7A and FIG. 7B of WO2014120770, the contents of which are herein incorporated by reference in its entirety), shows the differences in htCBS C15S (FIG. 5G, left panel) and htCBS dimer/tetramer ratio (FIG. 5G, right panel). The single peak for the dimeric C15S htCBS mutant eluted at 8.62 min while the main peak for the htCBS eluted at 7.9 min, corresponding to a tetramer. FIG. 4H shows a Coomassie-stained SDS-PAGE gel showing reproducibility of htCBS C15S PEGylation between different batches and comparison to htCBS. The absence of aggregates in the C15S htCBS resulted in a more consistent PEGylation pattern between different batches with almost exclusively one PEGylated band that appears on SDS-PAGE. Direct comparison between PEGhtCBS and the PEGC15S both in vivo and in vitro showed no difference in performance.

Figures 6A, 6B:
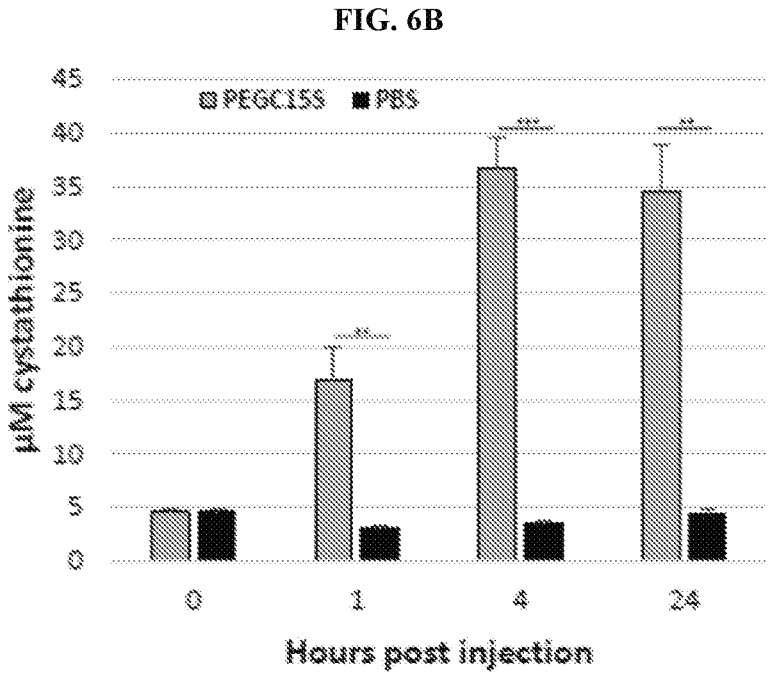
FIG. 6A-6C show the effect of PEGylated htCBS mutant (also referred to as PEGC15S) on homocysteine and its metabolites at 1, 4 and 24 hours post injection.
Figure 6C:
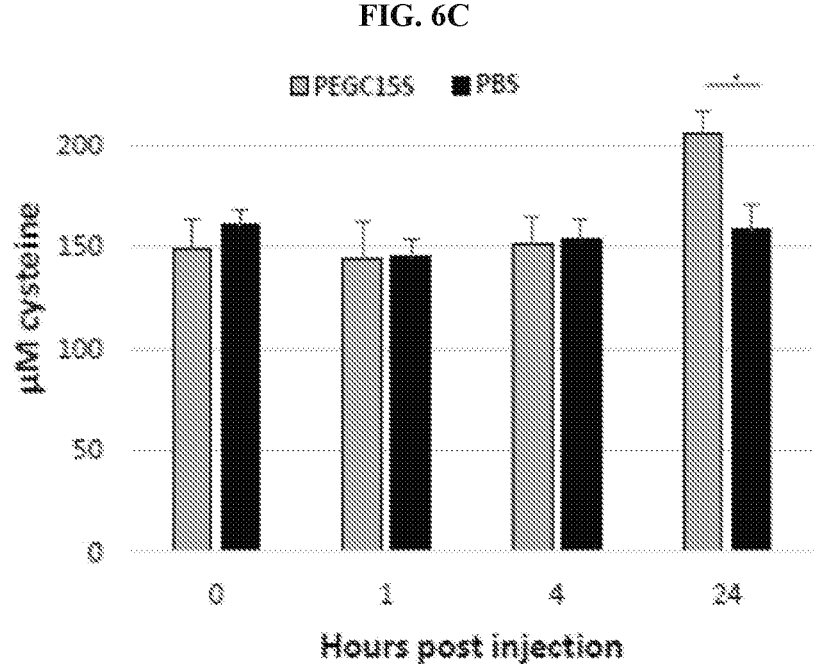

The effect of PEGC15S on metabolites was also tested at 1, 4 and 24 hours post injection (FIG. 6A-FIG. 6C). The levels of tHcy (FIG. 6A), cystathionine (FIG. 6B), and cysteine (FIG. 6C) in HO mice injected with 7.5 mg/kg of PEGC15S or PBS (n=5) 1, 4 and 24 hours post injection were measured. Data is presented as mean±SEM and each time point is compared between the two groups using unpaired Student's t test. *p=0.05, p≤0.01, and *p≤0.001. The effect on tHcy and cysteine was observed only 24 hours post injection (FIG. 6A and FIG. 6C), however a significant increase in cystathionine was already observed at 1 and 4 hours post injection (FIG. 6B).

Example 5. PEGC15S and Betaine Operate Synergistically in Vivo

To evaluate the effect of betaine and the combination therapy, betaine, PEGC15S, and a combination of betaine+PEGC15S treatments were conducted and metabolites of the transsulfuration pathway were compared.

Figure 7A:
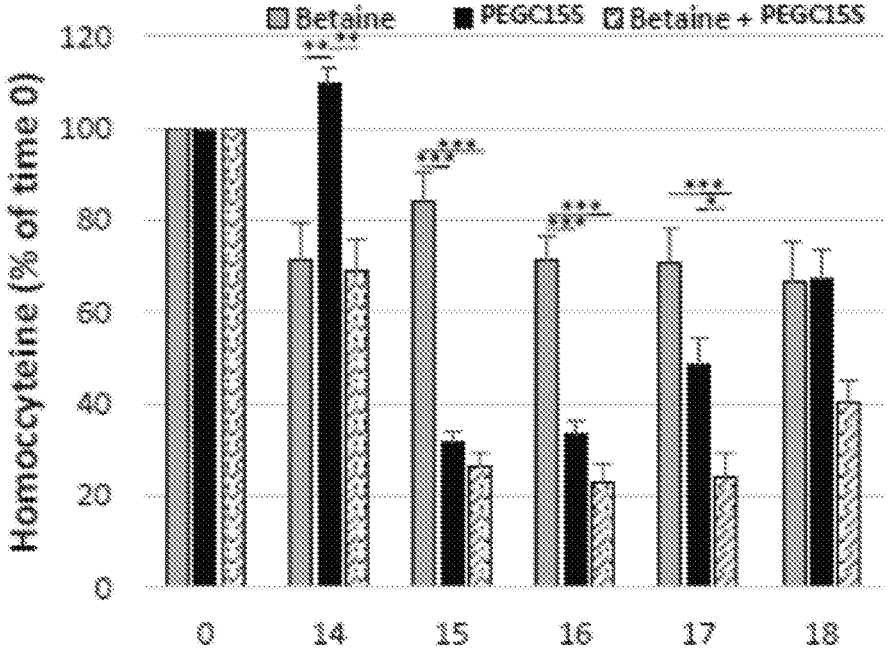
FIG. 7A-7B show that treatment with PEGylated htCBS mutant (also referred to as PEGC15S) and betaine synergistically reduce and maintain low homocysteine levels in HO mice and their effect on cystathionine levels.
Figure 7B:
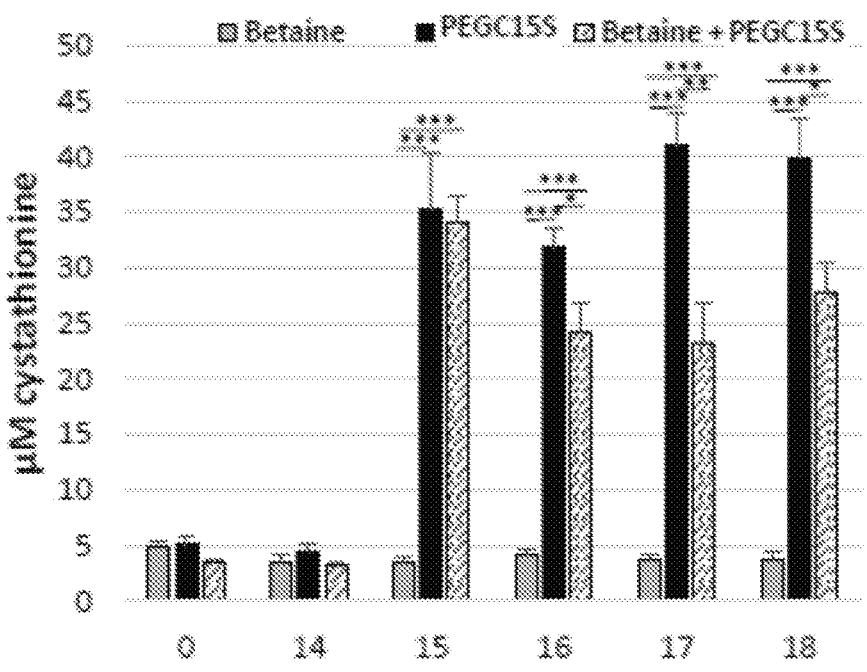

The betaine and betaine+PEGC15S groups were treated with 2% betaine in the drinking water throughout the 18 days of the experiment, and the latter group was injected with 7.5 mg/kg PEGC15S on days 14 and 15. The PEGC15S single treatment group was maintained on regular water and injected on days 14 and 15 as well. As shown in FIG. 7A, 14 days of betaine treatment resulted in a 29% and 32% decrease in tHcy for the betaine treated groups. The betaine single treatment group maintained these levels of tHcy to day 18. Injection of the PEGC15S on the background of betaine resulted in a more pronounced reduction of 74%, 77%, 76% and 40% on days 15, 16, 17 and 18, respectively. Treatment with PEGC15S alone resulted in a reduction of 69%, 67%, 52% and 33% on days 15, 16, 17 and 18, respectively. According to these data, injection of PEGC15S with or without betaine treatment is far superior to betaine treatment alone. In addition, the combination of betaine+PEGC15S was superior to treatment with PEGC15S alone. As shown in FIG. 7B, the difference between these two groups became statistically significant 48 hours post second injection (on day 17). Thus, the combination of PEGC15S with betaine allows for maintaining lower tHcy levels for an extended period of time.

Betaine treatment alone did not result in an increase of cystathionine throughout the 18 days of the experiment. In contrast, an increase was observed for the two groups that were treated with the PEGC15S (with or without betaine). Interestingly, the combination of PEGC15S with betaine, resulted in an increase which starting on day 16 and on, was significantly lower than in the group that received PEGC15S single therapy. This is due to the fact that treatment with PEGC15S alone channels homocysteine to condensation with serine to form cystathionine. Combination with betaine channels some of the available homocysteine through the re-methylation pathway to produce methionine, and thus less homocysteine may be available for PEGC15S to be converted to cystathionine.

Figure 8A:
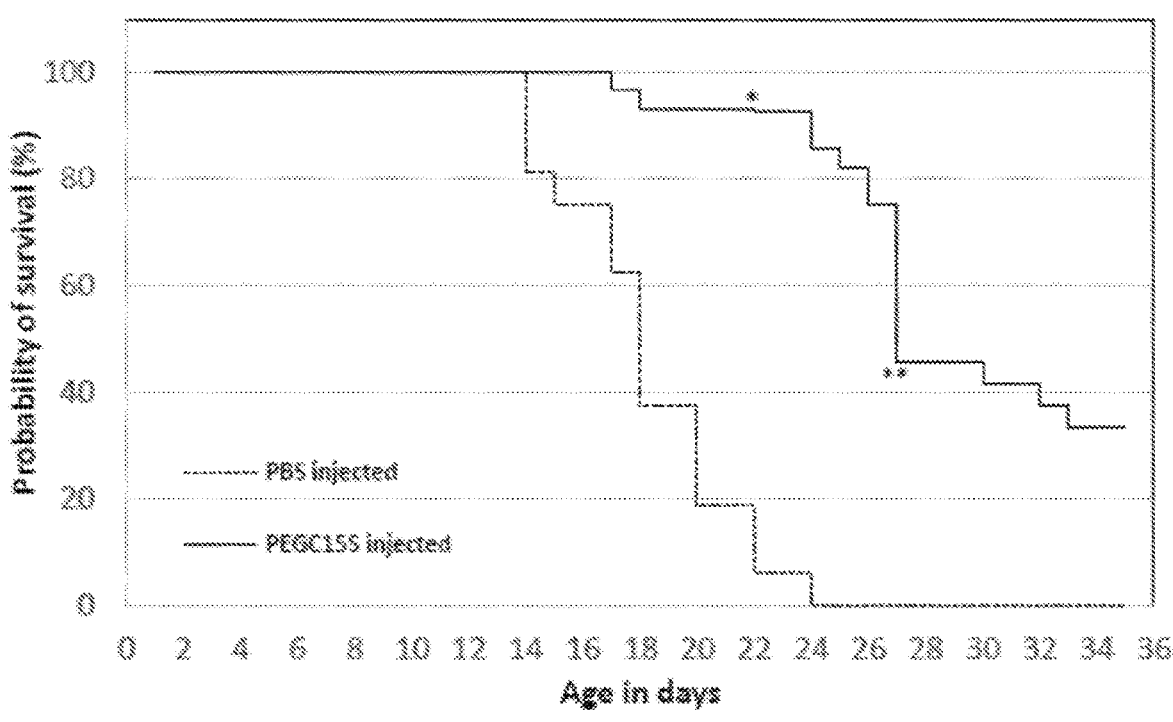
FIG. 8A-8B show that PEGylated htCBS mutant (also referred to as PEGC15S) administration rescues CBS complete knockout mice from early lethality and ameliorates liver pathology.

Example 6. PEGC15S Rescues KO Mice From Early Death and Improves Liver Disease A. Reduction of Early Death The majority of complete CBS-knockout mice (KOs) die within 2-3 weeks after birth. A Kaplan Meyer survival curve of KO mice injected twice weekly with PEGC15S versus mice that were injected with PBS was plotted. Mice were maintained on betaine water until day 21, and the ability of the injected enzyme to rescue KO pups was tested. KO pups were injected twice weekly with PEGC15S or with PBS. All mice were on betaine in drinking water up to day 21 (weaning day). As shown in FIG. 8A, on day 21, only 18% of the mice survived in the PBS-injected group as opposed to 93% of those that were injected with the enzyme. No PBS-injected animal survived to day 24, while 86% survival was recorded for the enzyme-injected group. From day 24 and on, the numbers of the enzyme-injected animals began to decline as well, with 45% survival on day 29 and 33% on day 35.

B. Liver Disease

It was previously demonstrated that KO mice suffer severe liver damage (Maclean et al., 2010a, *Mol. Genet. Metab* 101, 163-171; Watanabe et al., 1995, *Proc. Natl. Acad. Sci. U.S. A.* 92:1585-1589). Prolonged survival of KO mice, may be thus correlated with improvement in liver disease after CBS treatment. Accordingly, histological analysis of liver sections from animals that were injected with PEGC15S for 35 days were performed. Animals were sacrificed on day 36 and liver samples were processed for histological analysis by optical microscopy. PBS-injected animals did not survive to day 35, but liver samples were taken from two animals immediately after death, and were processed. The experiments were carried out in a blinded fashion. Livers were removed and were fixed for 24 hours with 4% paraformaldehyde in PBS (pH 7.4). Tissue blocks for histology were trimmed, dehydrated with an ethanol series followed by acetone, acetone-xylene mixture and xylene and then embedded in paraffin. In parallel, small tissue blocks (around 4 mm×2 mm) fixed with paraformaldehyde were rapidly frozen in petrol ether cooled with dry ice, and stored at −50° C. for detection of apolar lipids. Paraffin sections 4 μm thick were deparaffinized in xylene and after isopropyl alcohol step rehydrated with ethanol (96%, 70%, 60%). Tissue sections were stained with hematoxylin and eosin (H&E) to evaluate histopathological changes. Masson trichrome staining was performed for detection of fibrosis. Steatosis was verified using Oil Red O staining for detection of apolar lipids in fixed-frozen sections, 10 μm thick and cut with a Leica Cryomicrotome (CM 1850). The sections were viewed and photographed in a Nikon light microscope (E800) equipped with Olympus digital camera (DP70).

Figure 8B:
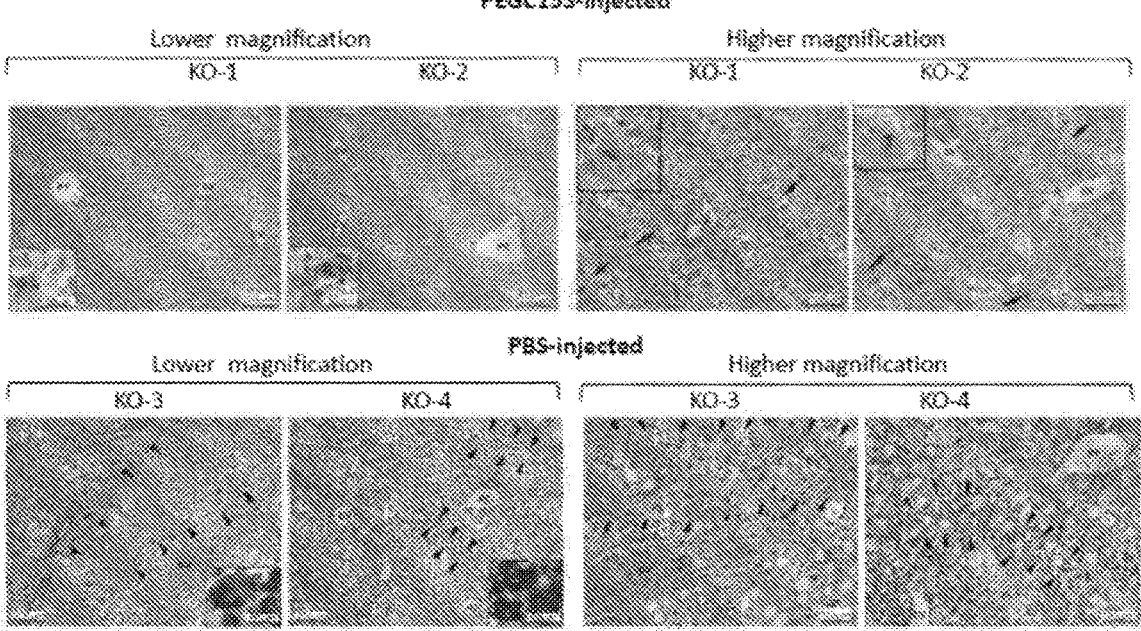

FIG. 8B shows the liver histology of two PEGC15S-injected KO mice sacrificed on day 35 versus livers from two PBS-injected KO animals that died on days 17 and 24 (hematoxylin and eosin stain). Low power views of the liver parenchyma (FIG. 8B, left columns) show moderate changes with slightly irregular liver cell plates and mild to moderate steatosis in PEGC15S-injected KO-1 and KO-2 contrasting with massive zonal necroses of hepatocytes (FIG. 8B, KO-3, marked by arrowheads) and diffuse steatosis with multiple dispersed necroses (FIG. 8B, KO-4, necroses marked by arrowheads) in PBS-injected KOs. A specific stain for apolar lipids in the cytoplasm of hepatocytes is shown in the inserts. Higher power views (right columns) demonstrate presence of frequent mitoses (marked by arrows and showed in a detail in inserts) and enlarged pleiomorphic nuclei with prominent nucleoli in PEGC15S-injected KOs. Higher power views of the liver parenchyma in PBS-injected KOs demonstrate confluent hepatocellular necroses with a sparse inflammatory infiltration (FIG. 8B, KO-3, marked by arrowheads) or multiple dispersed necroses accompanied with a prominent resorptive inflammatory reaction (FIG. 8B, KO-4, marked by arrowheads). The remaining liver parenchyma displays micro and macrovesicular steatosis in PBS-injected KOs. (PT=portal tract, CV=central vein).

PBS-injected animals developed severe hepatopathy characterized by pronounced microvesicular to macrovesicular steatosis and significant death of hepatocytes, with minimal or no fibrosis. Multiple mono or oligo cellular necroses of hepatocytes dispersed throughout the liver lobule accompanied by a prominent inflammatory resorptive reaction were found in one animal, whereas massive confluent necroses of hepatocytes mainly in periportal zones with a sparse inflammatory infiltrate dominated a feature in the other. Signs of liver parenchyma regeneration were minimal in both animals. The two PEGC15S-injected animals showed moderate changes in the liver with minor signs of parenchyma damage but with prominent regeneration, and were correctly recognized by the examiner as receiving therapy. Changes indicative of liver parenchyma regeneration (slightly irregular architecture of the liver lobule, basophilic cytoplasm of hepatocytes, frequent mitoses and binucleated hepatocytes, nuclear pleomorphy and enlargement with prominent nucleoli) were the most conspicuous feature. The overall morphology was consistent with increased proliferation, transcription and translation in hepatocytes. Besides, rare focal necroses of hepatocytes and mild steatosis of a microvesicular type were detected and fibrosis was minimal.

The foregoing examples of the related art and limitations related therewith are intended to be illustrative and not exclusive. Other limitations of the related art will become apparent to those of skill in the art upon a reading of the specification and a study of the drawings.

Compounds useful in the invention include those described herein in any of their pharmaceutically acceptable forms, including isomers such as diastereomers and enantiomers, salts, solvates, and polymorphs, as well as racemic mixtures and pure isomers of the compounds described herein, where applicable.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

All patents, patent applications, patent publications, scientific articles and the like, cited or identified in this application are hereby incorporated by reference in their entirety in order to describe more fully the state of the art to which the present application pertains.

We claim:

1. An isolated polypeptide dimer comprising two monomeric human truncated cystathionine β-synthase (htCBS) mutant polypeptide subunits, wherein each monomeric htCBS mutant polypeptide subunit independently comprises:

an amino acid sequence sharing an amino acid sequence identity of at least 80%, at least 90%, at least 95%, or at least 99% compared with SEQ ID NO:2, wherein the amino acid sequence of the htCBS mutant polypeptide further comprises a carboyxyl-terminal truncation, wherein the truncation comprises residues 383-551, 397-551, 414-551, 442-551, 489-551, 497-551, 524-551, 534-551, or 544-551 of SEQ ID NO: 2; and a mutation of a cysteine to a serine at amino acid position 15 (C15S) compared to a cystathionine β-synthase (CBS) protein comprising the amino acid sequence of SEQ ID NO: 2;

wherein each htCBS mutant polypeptide subunit is independently covalently linked to at least one polyethylene glycol (PEG) molecule, wherein the at least one PEG molecule is an NHS ester-activated PEG molecule or has a molecular weight greater than or equal to 20 kDa.

2. The isolated polypeptide dimer of claim 1, wherein each monomeric htCBS mutant polypeptide subunit independently comprises an amino acid sequence sharing an amino acid sequence identity of at least 99% compared with SEQ ID NO: 2.

3. The isolated polypeptide dimer of claim 1, wherein the carboxyl-terminated truncation of each monomeric htCBS mutant polypeptide subunit comprises residues 414-551 of SEQ ID NO: 2.

4. The isolated polypeptide dimer of claim 1, wherein each monomeric htCBS mutant polypeptide subunit is independently covalently linked to a plurality of PEG molecules, wherein each PEG molecule is an NHS ester-activated PEG molecule having a molecular weight greater than or equal to 20 kDa.

5. The isolated polypeptide dimer of claim 1, wherein each PEG molecule covalently linked to each htCBS mutant polypeptide subunit is independently an unbranched PEG molecule or a branched PEG molecule.

6. An isolated polypeptide dimer comprising two monomeric human truncated cystathionine β-synthase (htCBS) mutant polypeptide subunits, wherein each monomeric htCBS mutant polypeptide subunit independently comprises an amino acid sequence sharing an amino acid sequence identity of at least 99% compared with SEQ ID NO: 13, wherein each htCBS mutant polypeptide subunit is independently covalently linked to at least one 20 kDa NHS ester-actived PEG molecule.

7. The isolated polypeptide dimer of claim 6, wherein each monomeric htCBS mutant polypeptide subunit independently comprises amino acids 2-413 of the amino acid sequence of SEQ ID NO: 13.

8. The isolated polypeptide dimer of claim 7, wherein each monomeric htCBS mutant polypeptide subunit is independently covalently linked to a plurality of independent 20 kDa NHS ester-actived PEG molecules.

9. The isolated polypeptide dimer of claim 8, wherein the polypeptide dimer is purified from other protein components such that the polypeptide dimer comprises at least about 80% weight/weight of the total protein in a given composition, at least about 85% weight/weight of the total protein in a given composition, at least about 90% weight/weight of the total protein in a given composition, at least about 91% weight/weight of the total protein in a given composition, at least about 92% weight/weight of the total protein in a given composition, at least about 93% weight/weight of the total protein in a given composition, at least about 94% weight/weight of the total protein in a given composition, at least about 95% weight/weight of the total protein in a given composition, at least about 96% weight/weight of the total protein in a given composition, at least about 97% weight/weight of the total protein in a given composition, at least about 98% weight/weight of the total protein in a given composition, or at least about 99 weight/weight of the total protein in a given composition.

10. The isolated polypeptide dimer of claim 9, wherein the isolated polypeptide dimer is non-heme binding and remains catalytically active.

11. A pharmaceutical composition comprising:
   a therapeutically effective amount of the isolated polypeptide dimer of claim 8; and
   a pharmaceutically acceptable carrier, diluent, or excipient.

12. A method for treating or ameliorating a disease, disorder, or condition associated with elevated homocysteine in a subject in need thereof, the method comprising administering to the subject a therapeutically effective amount of the isolated polypeptide dimer of claim 8 or a pharmaceutical composition of claim 11.

13. A method for increasing the amount of a metabolite in a subject in need thereof, the method comprising administering to the subject a therapeutically effective amount of the isolated polypeptide dimer of claim 8 or a pharmaceutical composition of claim 11, wherein the metabolite is cystathionine or cysteine.

14. A method for decreasing the amount of a metabolite in a subject in need thereof, the method comprising administering to the subject a therapeutically effective amount of the isolated polypeptide dimer of claim 8 or a pharmaceutical composition of claim 11, wherein the metabolite is homocysteine, methionine, or S-adenosyl homocysteine.

15. A method for treating liver disease in a subject in need thereof, the method comprising administering to the subject a therapeutically effective amount of the isolated polypeptide dimer of claim 8 or a pharmaceutical composition of claim 11.

16. A method for treating homocystinuria or homocysteine remethylation disorder in a subject in need thereof, the method comprising administering to the subject a therapeutically effective amount of the isolated polypeptide dimer of claim 8 or a pharmaceutical composition of claim 11.

17. The method of claim 16, wherein the homocystinuria or homocysteine remethylation disorder is mental retardation, osteoporosis, ectopia lentis, kyphoscoliosis, stroke, myocardial infarction, or pulmonary embolism.

18. The method of claim 16, wherein the subject in need is also administered one or more of an anti-coagulant, a statin, a relaxed protein restricted diet, anethole dithiolethione, or betaine.

19. The method of claim 18, wherein betaine is administered twice daily.

20. The method of claim 18, wherein the individual is on a relaxed protein restricted diet.

21. The method of claim 16, wherein the isolated polypeptide dimer is administered to the subject in need thereof by an implanted osmotic pump, intravenous administration, subcutaneous administration, or intraperitoneal administration.

* * * * *

SEQUENCE LISTING

Sequence total quantity: 16
SEQ ID NO: 1              moltype = DNA   length = 1656
FEATURE                   Location/Qualifiers
source                    1..1656
                          mol_type = genomic DNA
                          organism = Homo sapiens
SEQUENCE: 1
atgccgtcag aaaccccgca ggcagaagtg ggtccgacgg gttgcccgca ccgtagcggt    60
ccgcattctg caaaaggcag tctggaaaaa ggttccccgg aagataaaga agccaaagaa   120
ccgctgtgga ttcgtccgga cgcaccgtca cgctgtacct ggcagctggg tcgtccggca   180
agcgaatctc cgcatcacca tacggctccg gcgaaaagtc cgaaaattct gccggatatc   240
ctgaagaaaa ttggtgacac cccgatggtt cgtatcaaca aaatcggcaa aaaattcggt   300
ctgaaatgcg aactgctggc taaatgtgaa tttttcaatg cgggcggttc cgtgaaagat   360
cgtatctcac tgcgcatgat tgaagatgct gaacgcgacg gcaccctgaa accgggtgat   420
acgattatcg aaccgacctc tggcaacacg ggtatcggtc tggcactggc ggcggcagtc   480
cgtggttatc gctgcattat cgtgatgccg gaaaaaatga gctctgaaaa agttgatgtc   540
ctgcgtgctc tgggcgcgga aattgttcgt accccgacga atgcccgctt cgacagtccg   600
gaatcccatg tgggtgttgc atggcgcctg aaaaacgaaa tcccgaattc gcacattctg   660
gatcagtatc gtaacgctag caatccgctg gcgcattaca tacacggc cgacgaaatc   720
ctgcagcaat gtgatggcaa actggacatg ctggtcgctt ctgtgggtac cggcggtacc   780
attacgggca tcgcgcgtaa actgaaagaa aaatgcccgg gctgtcgcat tatcggtgtg   840
gatccggaag gcagtattct ggcggaaccg gaagaactga accagaccga acaaaccacg   900
tatgaagttg aaggcatcgg ttacgatttt attccgaccg tacctggatcg cacggtggtt   960
gacaaatggt tcaaaagcaa tgacgaagaa gcctttacct tcgcacgtat gctgatcgct  1020
caggaaggtc tgctgtgcgg tggttcagca ggttcgacgg tcgcagtggc agttaaagct  1080
gcgcaggaac tgcaagaagg tcaacgttgt gtcgtgattc tgccggattc tgttcgcaac  1140
tacatgacca aatttctgag tgaccgttgg atgctgcaaa aaggcttcct gaaagaagaa  1200
gatctgaccg agaaaaaacc gtggtggtgg cacctgcgcg tgcaggaact gggtctgtcc  1260
gcaccgctga ccgttctgcc gaccatcacg tgcggccata cgattgaaat cctgcgtgaa  1320
aaaggttttg atcaggcccc ggttgtcgac gaagcaggcg tgattctggg tatggttacc  1380
ctgggtaaca tgctgagttc cctgctggcg ggcaaagtgc aaccgagcga tcaggttggt  1440
aaagtcatct acaaacaatt caaacagatt cgtctgacga tacgctggg ccgcctgtcg  1500
cacatcctgg aaatggacca tttcgcgctg gttgtgcacg aacagattca ataccatagc  1560
accggcaaat catcgcagcg ccaaatggtc tttggtgtcg tgacggccat tgatctgctg  1620
aatttcgtgg ccgcacaaga acgtgaccag aaataa                            1656

SEQ ID NO: 2              moltype = AA   length = 551
FEATURE                   Location/Qualifiers
source                    1..551
                          mol_type = protein
                          organism = Homo sapiens
SEQUENCE: 2
MPSETPQAEV GPTGCPHRSG PHSAKGSLEK GSPEDKEAKE PLWIRPDAPS RCTWQLGRPA    60
SESPHHHTAP AKSPKILPDI LKKIGDTPMV RINKIGKKFG LKCELLAKCE FFNAGGSVKD   120
RISLRMIEDA ERDGTLKPGD TIIEPTSGNT GIGLALAAAV RGYRCIIVMP EKMSSEKVDV   180
LRALGAEIVR TPTNARFDSP ESHVGVAWRL KNEIPNSHIL DQYRNASNPL AHYDTTADEI   240
LQQCDGKLDM LVASVGTGGT ITGIARKLKE KCPGCRIIGV DPEGSILAEP EELNQTEQTT   300
YEVEGIGYDF IPTVLDRTVV DKWFKSNDEE AFTFARMLIA QEGLLCGGSA GSTVAVAVKA   360
AQELQEGQRC VVILPDSVRN YMTKFLSDRW MLQKGFLKEE DLTEKKPWWW HLRVQELGLS   420
APLTVLPTIT CGHTIEILRE KGFDQAPVVD EAGVILGMVT LGNMLSSLLA GKVQPSDQVG   480
KVIYKQFKQI RLTDTLGRLS HILEMDHFAL VVHEQIQYHS TGKSSQRQMV FGVVTAIDLL   540
NFVAAQERDQ K                                                        551

SEQ ID NO: 3              moltype = AA   length = 413
FEATURE                   Location/Qualifiers
REGION                    1..413
                          note = Synthetic
source                    1..413
                          mol_type = protein
                          organism = synthetic construct
SEQUENCE: 3
MPSETPQAEV GPTGCPHRSG PHSAKGSLEK GSPEDKEAKE PLWIRPDAPS RCTWQLGRPA    60
SESPHHHTAP AKSPKILPDI LKKIGDTPMV RINKIGKKFG LKCELLAKCE FFNAGGSVKD   120
RISLRMIEDA ERDGTLKPGD TIIEPTSGNT GIGLALAAAV RGYRCIIVMP EKMSSEKVDV   180
LRALGAEIVR TPTNARFDSP ESHVGVAWRL KNEIPNSHIL DQYRNASNPL AHYDTTADEI   240
LQQCDGKLDM LVASVGTGGT ITGIARKLKE KCPGCRIIGV DPEGSILAEP EELNQTEQTT   300
YEVEGIGYDF IPTVLDRTVV DKWFKSNDEE AFTFARMLIA QEGLLCGGSA GSTVAVAVKA   360
AQELQEGQRC VVILPDSVRN YMTKFLSDRW MLQKGFLKEE DLTEKKPWWW HLR           413

SEQ ID NO: 4              moltype = DNA   length = 1242
FEATURE                   Location/Qualifiers
misc_feature             1..1242
                          note = Synthetic
source                    1..1242
                          mol_type = other DNA
                          organism = synthetic construct
SEQUENCE: 4
atgccgtcag aaaccccgca ggcagaagtg ggtccgacgg gttgcccgca ccgtagcggt    60

-continued

```
ccgcattctg caaaaggcag tctggaaaaa ggttccccgg aagataaaga agccaaagaa   120
ccgctgtgga ttcgtccgga cgcaccgtca cgctgtacct ggcagctggg tcgtccggca   180
agcgaatctc cgcatcacca tacggctccg gcgaaaagtc cgaaaattct gccggatatc   240
ctgaagaaaa ttggtgacac cccgatggtt cgtatcaaca aaatcggcaa aaaattcggt   300
ctgaaatgcg aactgctggc taaatgtgaa tttttcaatg cgggcggttc cgtgaaagat   360
cgtatctcac tgcgcatgat tgaagatgct gaacgcgacg gcaccctgaa accgggtgat   420
acgattatcg aaccgacctc tggcaacacg ggtatcggtc tggcactggc ggcggcagtc   480
cgtggttatc gctgcattat cgtgatgccg gaaaaaatga gctctgaaaa agttgatgtc   540
ctgcgtgctc tgggcgcgga aattgttcgt accccgacga atgcccgctt cgacagtccg   600
gaatcccatg tgggtgttgc atggcgcctg aaaaacgaaa tcccgaattc gcacattctg   660
gatcagtatc gtaacgctag caatccgctg cgcgcattacg ataccacggc cgacgaaatc   720
ctgcagcaat gtgatggcaa actggacatg ctggtcgctt ctgtgggtac cggcggtacc   780
attacgggca tcgcgcgtaa actgaaagaa aaatgcccgg gctgtcgcat tatcggtgtg   840
gatccggaag gcagtattct ggcggaaccg gaagaactga accagaccga acaaaccacg   900
tatgaagttg aaggcatcgg ttacgatttt attccgaccg tcctggatcg cacggtggtt   960
gacaaatggt tcaaaagcaa tgacgaagaa gcctttacct tcgcacgtat gctgatcgct   1020
caggaaggtc tgctgtgcgg tggttcagca ggttcgacgg tcgcagtggc agttaaagct   1080
gcgcaggaac tgcaagaagg tcaacgttgt gtcgtgattc tgccggattc tgttcgcaac   1140
tacatgacca aatttctgag tgaccgttgg atgctgcaaa aaggcttcct gaaagaagaa   1200
gatctgaccg agaaaaaacc gtggtggtgg cacctgcgct aa   1242
```

```
SEQ ID NO: 5           moltype = DNA  length = 30
FEATURE                Location/Qualifiers
misc_feature           1..30
                       note = Synthetic oligonucleotide
source                 1..30
                       mol_type = other DNA
                       organism = synthetic construct
SEQUENCE: 5
cgtagaattc acctttgccc gcatgctgat                                    30

SEQ ID NO: 6           moltype = DNA  length = 35
FEATURE                Location/Qualifiers
misc_feature           1..35
                       note = Synthetic oligonucleotide
source                 1..35
                       mol_type = other DNA
                       organism = synthetic construct
SEQUENCE: 6
tacgggtacc tcaacggagg tgccaccacc agggc                              35

SEQ ID NO: 7           moltype = DNA  length = 29
FEATURE                Location/Qualifiers
misc_feature           1..29
                       note = Synthetic oligonucleotide
source                 1..29
                       mol_type = other DNA
                       organism = synthetic construct
SEQUENCE: 7
agtcgcccat ggcgtcagaa accccgcag                                     29

SEQ ID NO: 8           moltype = DNA  length = 31
FEATURE                Location/Qualifiers
misc_feature           1..31
                       note = Synthetic oligonucleotide
source                 1..31
                       mol_type = other DNA
                       organism = synthetic construct
SEQUENCE: 8
atcgcgctcg agttagcgca ggtgccacca c                                  31

SEQ ID NO: 9           moltype = DNA  length = 30
FEATURE                Location/Qualifiers
misc_feature           1..30
                       note = Synthetic oligonucleotide
source                 1..30
                       mol_type = other DNA
                       organism = synthetic construct
SEQUENCE: 9
ggagatatac catgccgtca gaaaccccgc                                    30

SEQ ID NO: 10          moltype = DNA  length = 30
FEATURE                Location/Qualifiers
misc_feature           1..30
                       note = Synthetic oligonucleotide
source                 1..30
                       mol_type = other DNA
                       organism = synthetic construct
SEQUENCE: 10
```

```
gcggggtttc tgacggcatg gtatatctcc                                           30

SEQ ID NO: 11              moltype = DNA   length = 23
FEATURE                    Location/Qualifiers
misc_feature               1..23
                           note = Synthetic oligonucleotide
source                     1..23
                           mol_type = other DNA
                           organism = synthetic construct
SEQUENCE: 11
tgggtccgac gggtagcccg cac                                                  23

SEQ ID NO: 12              moltype = DNA   length = 23
FEATURE                    Location/Qualifiers
misc_feature               1..23
                           note = Synthetic oligonucleotide
source                     1..23
                           mol_type = other DNA
                           organism = synthetic construct SEQUENCE: 12
gtgcgggcta cccgtcggac cca                                                  23

SEQ ID NO: 13              moltype = AA   length = 413
FEATURE                    Location/Qualifiers
REGION                     1..413
                           note = Truncated human C15S mutant CBS polypeptide
source                     1..413
                           mol_type = protein
                           organism = synthetic construct
SEQUENCE: 13
MPSETPQAEV GPTGSPHRSG PHSAKGSLEK GSPEDKEAKE PLWIRPDAPS RCTWQLGRPA     60
SESPHHHTAP AKSPKILPDI LKKIGDTPMV RINKIGKKFG LKCELLAKCE FFNAGGSVKD     120
RISLRMIEDA ERDGTLKPGD TIIEPTSGNT GIGLALAAAV RGYRCIIVMP EKMSSEKVDV     180
LRALGAEIVR TPTNARFDSP ESHVGVAWRL KNEIPNSHIL DQYRNASNPL AHYDTTADEI     240
LQQCDGKLDM LVASVGTGGT ITGIARKLKE KCPGCRIIGV DPEGSILAEP EELNQTEQTT     300
YEVEGIGYDF IPTVLDRTVV DKWFKSNDEE AFTFARMLIA QEGLLCGGSA GSTVAVAVKA     360
AQELQEGQRC VVILPDSVRN YMTKFLSDRW MLQKGFLKEE DLTEKKPWWW HLR            413

SEQ ID NO: 14              moltype = DNA   length = 1242
FEATURE                    Location/Qualifiers
misc_feature               1..1242
                           note = Truncated human C15S mutant CBS Nucleotide
source                     1..1242
                           mol_type = other DNA
                           organism = synthetic construct
SEQUENCE: 14
atgccgtcag aaaccccgca ggcagaagtg ggtccgacgg gtagcccgca ccgtagcggt     60
ccgcattctg caaaaggcag tctggaaaaa ggttccccgg aagataaaga agccaaagaa     120
ccgctgtgga ttcgtccgga cgcaccgtca cgctgtacct ggcagctggg tcgtccggca     180
agcgaatctc cgcatcacca tacggctccg gcgaaaagtc cgaaaattct gccggatatc     240
ctgaagaaaa ttggtgacac cccgatggtt cgtatcaaca aaatcggcaa aaaattcggt     300
ctgaaatgcg aactgctggc taaatgtgaa ttttttcaatg cgggcggttc cgtgaaagat     360
cgtatctcac tgcgcatgat tgaagatgct gaacgcgacg gcaccctgaa accgggtgat     420
acgattatcg aaccgacctc tggcaacacg ggtatcggtc tggcactggc ggcggcagtc     480
cgtggttatc gctgcattat cgtgatgccg gaaaaaatga gctctgaaaa agttgatgtc     540
ctgcgtgctc tgggcgcgga aattgttcgt accccgacga atgcccgctt cgacagtccg     600
gaatcccatg tgggtgttgc atggcgcctg aaaaacgaaa tcccgaattc gcacattctg     660
gatcagtatc gtaacgctag caatccgctg gcgcattacg ataccacggc cgacgaaatc     720
ctgcagcaat gtgatggcaa actggacatg ctggtcgctt ctgtgggtac cggcggtacc     780
attacgggca tcgcgcgtaa actgaaagaa aaatgcccgg gctgtcgcat tatcggtgtg     840
gatccggaag gcagtattct ggcggaaccg gaagaactga accagaccga acaaaccacg     900
tatgaagtta aaggcatcgg ttacgatttt attccgaccg tcctggatcg cacggtggtt     960
gacaaatggt tcaaaagcaa tgacgaagaa gcctttacct cgcacgtat gctgatcgct     1020
caggaaggtc tgctgtgcgg tggttcagca ggttcgaccg tcgcagtggc agttaaagct     1080
gcgcaggaac tgcaagaagg tcaacgttgt gtcgtgattc tgccggattc tgttcgcaac     1140
tacatgacca aatttctgag tgaccgttgg atgctgcaaa aaggcttcct gaaagaagaa     1200
gatctgaccg agaaaaaacc gtggtggtgg cacctgcgct aa                         1242

SEQ ID NO: 15              moltype = DNA   length = 1656
FEATURE                    Location/Qualifiers
misc_feature               1..1656
                           note = Full length human C15S mutant CBS nucleotide
source                     1..1656
                           mol_type = other DNA
                           organism = synthetic construct
SEQUENCE: 15
atgccgtcag aaaccccgca ggcagaagtg ggtccgacgg gtagcccgca ccgtagcggt     60
ccgcattctg caaaaggcag tctggaaaaa ggttccccgg aagataaaga agccaaagaa     120
ccgctgtgga ttcgtccgga cgcaccgtca cgctgtacct ggcagctggg tcgtccggca     180
```

-continued

```
agcgaatctc cgcatcacca tacggctccg gcgaaaagtc cgaaaattct gccggatatc  240
ctgaagaaaa ttggtgacac cccgatggtt cgtatcaaca aaatcggcaa aaaattcggt  300
ctgaaatgcg aactgctggc taaatgtgaa tttttcaatg cgggcggttc cgtgaaagat  360
cgtatctcac tgcgcatgat tgaagatgct gaacgcgacg gcaccctgaa accgggtgat  420
acgattatcg aaccgacctc tggcaacacg ggtatcgtct tggcactggc ggcggcagtc  480
cgtggttatc gctgcattat cgtgatgccg gaaaaaatga gctctgaaaa agttgatgtc  540
ctgcgtgctc tgggcgcgga aattgttcgt accccgacga atgcccgctt cgacagtccg  600
gaatcccatg tgggtgttgc atggcgcctg aaaaacgaaa tcccgaattc gcacattctg  660
gatcagtatc gtaacgctag caatccgctg gcgcattacg ataccacggc cgacgaaatc  720
ctgcagcaat gtgatggcaa actggacatg ctggtcgctt ctgtgggtac cggcggtacc  780
attacgggca tcgcgcgtaa actgaaagaa aaatgcccgg gctgtcgcat tatcggtgtg  840
gatccggaag gcagtattct ggcggaaccg gaagaactga accagaccga acaaaccacg  900
tatgaagttg aaggcatcgg ttacgatttt attccgaccg tcctggatcg cacggtggtt  960
gacaaatggt tcaaaagcaa tgacgaagaa gcctttacct tcgcacgtat gctgatcgct  1020
caggaaggtc tgctgtgcgg tggttcagca ggttcgacgg tcgcagtggc agttaaagct  1080
gcgcaggaac tgcaagaagg tcaacgttgt gtcgtgattc tgccggattc tgttcgcaac  1140
tacatgacca aatttctgag tgaccgttgg atgctgcaaa aaggcttcct gaaagaagaa  1200
gatctgaccg agaaaaaacc gtggtggtgg cacctgcgcg tgcaggaact gggtctgtcc  1260
gcaccgctga ccgttctgcc gaccatcacg tgcggccata cgattgaaat cctgcgtgaa  1320
aaaggttttg atcaggcccc ggttgtcgac gaagcaggcg tgattctggg tatggttacc  1380
ctgggtaaca tgctgagttc cctgctggcg ggcaaagtgc aaccgagcga tcaggttggt  1440
aaagtcatct acaaacaatt caaacagatt cgtctgaccg atacgctggg ccgcctgtcg  1500
cacatcctgg aaatggacca tttcgcgctg gttgtgcacg aacagattca ataccatagc  1560
accggcaaat catcgcagcg ccaaatggtc tttggtgtcg tgacggccat tgatctgctg  1620
aatttcgtgg ccgcacaaga acgtgaccag aaataa                            1656
```

```
SEQ ID NO: 16        moltype = AA  length = 551
FEATURE              Location/Qualifiers
REGION               1..551
                     note = Full length human C15S mutant CBS polypeptide
source               1..551
                     mol_type = protein
                     organism = synthetic construct
SEQUENCE: 16
MPSETPQAEV GPTGSPHRSG PHSAKGSLEK GSPEDKEAKE PLWIRPDAPS RCTWQLGRPA  60
SESPHHHTAP AKSPKILPDI LKKIGDTPMV RINKIGKKFG LKCELLAKCE FFNAGGSVKD  120
RISLRMIEDA ERDGTLKPGD TIIEPTSGNT GIGLALAAAV RGYRCIIVMP EKMSSEKVDV  180
LRALGAEIVR TPTNARFDSP ESHVGVAWRL KNEIPNSHIL DQYRNASNPL AHYDTTADEI  240
LQQCDGKLDM LVASVGTGGT ITGIARKLKE KCPGCRIIGV DPEGSILAEP EELNQTEQTT  300
YEVEGIGYDF IPTVLDRTVV DKWFKSNDEE AFTFARMLIA QEGLLCGGSA GSTVAVAVKA  360
AQELQEGQRC VVILPDSVRN YMTKFLSDRW MLQKGFLKEE DLTEKKPWWW HLRVQELGLS  420
APLTVLPTIT CGHTIEILRE KGFDQAPVVD EAGVILGMVT LGNMLSSLLA GKVQPSDQVG  480
KVIYKQFKQI RLTDTLGRLS HILEMDHFAL VVHEQIQYHS TGKSSQRQMV FGVVTAIDLL  540
NFVAAQERDQ K                                                       551
```